United States Patent
Miyano et al.

(10) Patent No.: US 7,148,069 B2
(45) Date of Patent: Dec. 12, 2006

(54) METHOD FOR ANALYSIS OF COMPOUNDS WITH AMINO GROUP AND ANALYTICAL REAGENT THEREFOR

(75) Inventors: Hiroshi Miyano, Kawasaki (JP); Akihisa Yahashi, Kawasaki (JP); Kazutaka Shimbo, Kawasaki (JP); Masakazu Nakazawa, Kawasaki (JP); Kazuo Hirayama, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/918,380

(22) Filed: Aug. 16, 2004

(65) Prior Publication Data
US 2005/0079624 A1 Apr. 14, 2005

Related U.S. Application Data

(63) Continuation of application No. PCT/JP03/01463, filed on Feb. 13, 2003.

(30) Foreign Application Priority Data
Feb. 14, 2002 (JP) .............................. 2002-036446

(51) Int. Cl.
*G01N 33/00* (2006.01)
*G01N 24/00* (2006.01)
*C07D 215/38* (2006.01)

(52) U.S. Cl. ............................ 436/96; 436/56; 436/86; 436/89; 436/91; 436/173; 530/409; 546/102; 546/159; 546/278.4; 548/364.1; 548/542

(58) Field of Classification Search .................... 436/8, 436/56, 63, 86, 89, 91, 96, 173; 530/409; 546/102, 159, 278.4; 548/364.1, 542
See application file for complete search history.

(56) References Cited

U.S. PATENT DOCUMENTS

| 5,296,599 | A |  | 3/1994 | Cohen et al. |
| 6,670,194 | B1 | * | 12/2003 | Aebersold et al. .......... 436/173 |
| 6,818,454 | B1 | * | 11/2004 | Goshe et al. ................ 436/173 |
| 6,902,936 | B1 | * | 6/2005 | Qiu et al. ...................... 436/86 |
| 6,905,879 | B1 | * | 6/2005 | Qiu et al. ...................... 436/86 |

FOREIGN PATENT DOCUMENTS

| JP | 2001-235477 | 8/2001 |
| WO | WO 00/11208 | 3/2000 |
| WO | WO 02/04936 | 1/2002 |

OTHER PUBLICATIONS

Liu et al. Journal of Chromatography A, vol. 927, 2001, pp. 77-89.*
Liu et al. Analytica Chimica Acta, vol. 400, 1999, pp. 181-209.*
T. Hirai, et al.,"Development of a New Fluorescence Labeling Reagent Succinimido-2-Fluorenylcarbamate for Highly Sensitive Detection of N-Solanesyl-N, N'-BIS (3,4-Dimethoxybenzyl)Ethanediamine by HPLC", Bunseki Kagaku, vol. 40, No. 5, May 5, 1991, pp. 233-238 (w/attached English Abstract).

* cited by examiner

*Primary Examiner*—Maureen M. Wallenhorst
(74) *Attorney, Agent, or Firm*—Oblon, Spivak, McClelland, Maier & Neustadt, P.C.

(57) ABSTRACT

The present invention provides a method for the analysis of a compound with amino group (e.g., an amino acid or peptide) contained in a sample and convenient manner with a high sensitivity. The compound with amino group in a sample containing the compound with amino group is labeled with a specific carbamate compound such as p-trimethylammonium anilyl-N-hydroxysuccinimidyl carbamate iodide to enhance the selectivity and sensitivity. The present invention is preferably used in conjunction with mass spectrometry such as MS/MS method to facilitate quantitative analysis. The present invention further provides labeling reagents for mass spectrometry.

35 Claims, 10 Drawing Sheets

METHOD FOR ANALYSIS OF COMPOUNDS WITH AMINO GROUP AND ANALYTICAL REAGENT THEREFOR

CROSS-REFERENCE TO RELATED APPLICATIONS

The present application is a continuation of International application PCT/JPO3/01463, filed on Feb. 13, 2003, which claims priority to Japanese Application No. JP 2002-036446, filed on Feb. 14, 2002, the entire contents of these applications are hereby incorporated by reference in their entirety.

BACKGROUND OF THE INVENTION

1. Field of the Invention

The present invention provides a method for the analysis (including detection) of a compound having an amino group, such as amino acid and peptide, by using mass spectrometry with a high sensitivity analytical reagent that enhances the selectivity of the compound. The present invention also provides an analytical (labeling) reagent that may be used for the aforementioned method; a method for the labeling a compound having an amino group; and a novel carbamate compound as the analytical reagent.

2. Discussion of the Background

Compounds with amino groups—including amino acids, peptides and others—play an important role in living body. In view of this importance, a critical demand exists in the fields of medicine, pharmaceutical science, agriculture, biochemistry and clinical chemistry to quantitate the relative abundance thereof. In particular, there is a critical demand for a selective and highly sensitive quantitative determination method for particularly amino acids, especially where the sample amount and the concentration of the analyte is varied and impurities are likely to be present. A typical example of where the demand exists is when amino acids of metabolites in cells are to be quantified. Moreover, by improving the selectivity and sensitivity of the quantitative method less sample amount is needed, thus reducing the physical and mental burden of the person to be tested.

Most amino acids have very low ultraviolet absorption, fluorescence and/or electrochemical response. Heretofore, to enhance the analytical sensitivity, a method where an amino group is labeled with compound, chromophore or fluorophore having a large ultraviolet absorptivity and is detected by ultraviolet, visible light or fluorescence has been usually used. In regard to a representative ultraviolet labeling reagent, phenylisothiocyanate (PITC) [cf. Cohen, S. A. and Strydom, D. J., 174, 1 (1988)] has been employed while ninhydrin has been widely known as a visible labeling reagent. Both of these reagents are commercially available. In regard to a fluorescence labeling reagent, o-phthalaldehyde (OPA) [cf. Roth, M., *Anal. Chem.* 43, 880 (1971)], dansyl chloride (Dansyl-Cl) [cf. Seiler, N., *Methods Biochem. Anal.,* 18, 259 (1970)], 4-fluoro-7-nitrobenzofurazan (NBD-F) [cf. Imai, K. and Watanabe, Y., *Anal. Chim. Acta,* 130, 377 (1981)], etc. have also been reported and are commercially available.

In the aforementioned analytical methods, the limit of the analytical sensitivity for ultraviolet/visible light is typically about 1 pmol, while amount of amino acid which can be detectable by using fluorescence is about 100 fmol. Thus, in the field of biochemistry and clinical chemistry, there has been a demand for further improvement in the sensitivity. Further, where labeling substances that have an absorption in an ultraviolet region (PITC; 254 nm) or labeling substance having excitation and fluorescence wavelength that are in relatively short wavelength (OPA: $(\lambda)ex=340$ to 345 nm, $(\lambda)em=455$ nm; Dansyl-Cl: $(\lambda)ex=255$ nm, $(\lambda)em=470$ nm), accurate quantification is frustrated by the presence of impurities.

Usually, to achieve a quantitative analytical result an excessive reagent quantity must be added to the analyte during the labeling reaction leading to a need for additional purification. If the purification step is omitted, the quantitative results are often difficult to accurately interpret since for many labeling substances (e.g., PITC, Dansyl-Cl and NBD-F) the reagent or a hydrolysate thereof has strong ultraviolet absorption and fluorescence. Therefore, the reagent or a hydrolysate thereof is a big impediment in the analysis.

6-Aminoquinolyl-N-hydroxysuccinimidyl carbamate (AQC) [cf. Iwaki, K., Yoshida, S., Nimura, N., Kinoshita, T., Takeda, K., and Ogura, H., *Chromatographia,* 23, 899 (1987)] has been also developed as a reagent to label an amino group of an amino acid to enable fluorescence detection. However, this reagent is plagued by the same problems discussed above in that its excitation wavelength and fluorescence wavelength are in a short wavelength range of $(\lambda)ex=245$ nm and $(\lambda)em=395$ nm, respectively. Therefore, AQC is apt to be affected by impurities. Moreover, the reagent and a hydrolysate thereof also have fluorescence properties.

As stated above, when the aforementioned labeling reagents are used a purification method where the labeled compound is separated by a liquid chromatography (hereinafter, referred to as HPLC) has been performed to analyze the amino acid. In the HPLC, there are many cases where retention ability of the substance to be analyzed in a column varies by slight changes in the environment or, in other words, by slight changes in the composition of the mobile phase or by changes in column temperature. Since detection is conducted by absorption or fluorescence of the labeling reagent, each amino acid should be identified by means of column-retention ability. When an analyte having unpredictable retention ability is detected, the fact that the substance has an amino group can be noted but any other information concerning the structure can not be ascertained.

Accordingly, the current state of the art in which analysis of a labeled compound with amino group by means of ultraviolet ray, visible ray, or fluorescence has another problem in the selectivity. Therefore, the present invention seeks to meet the critical demand for a selective and highly sensitive quantitative determination method for a compound having an amino group (e.g., amino acids), especially where the sample amount and the concentration of the analyte is varied and impurities are likely to be present.

SUMMARY OF THE INVENTION

It is an object of the present invention to provide a convenient, highly sensitive and selective method for the analysis of a compound with amino group (e.g., an amino acid).

In one object of the present invention is a carbamate compound (or a labeling reagent comprising the same) represented by the formula (1) comprising a stable isotope element on at least one atom contained in the structure O=C—NH—Ar

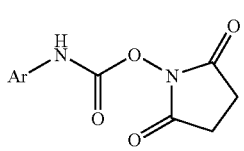

(1)

wherein Ar is a carbocyclic compound or a heterocyclic compound having an aromaticity where the aromatic ring may have one or more substituent(s), and wherein the bond between Ar group and nitrogen atom of a carbamate group, a carbon atom constituting the ring in the Ar group is bound to a nitrogen atom of the carbamate group, whereby the carbamate compound may be in a form of a salt with the proviso that that stable isotope element is not the exchangeable hydrogen atom.

In another object of the present invention is a carbamate compound (or a labeling reagent comprising the same) represented by formula (1)

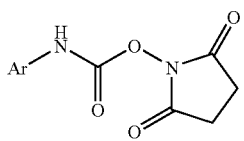

(1)

wherein Ar bound to a nitrogen atom of a carbamate group is a carbocyclic compound or heterocyclic compound residue having an aromaticity where a polar substituent is bound to the ring, or a pyridyl group, a pyrazyl group, or a quinolyl group where a polar substituent is not bound to the ring, with the proviso that the carbon atom at the 3, 5, or 6-position of said quinolyl group is not bound to a nitrogen atom of a carbamate group, and wherein the bond between Ar group and a nitrogen atom in the carbamate group, the carbon atom constituting the ring in Ar group is bound to a nitrogen atom of the carbamate group, whereby the carbamate compound may be in a form of a salt.

In yet another object of the present invention is a method for analyzing (and/or quantifying) a compound with an amino group in a sample containing at least a compound with amino group by means of mass spectrometry, comprising labeling said compound with an amino group in said sample by reacting said compound with an amino group with a carbamate compound (or labeling reagent containing the same) as described above for a time and under conditions suitable to facilitate said labeling providing a sample containing a compound with an amino group labeled with a carbamate compound having one or more of stable isotope, subjecting the labeled compound to mass spectrometry.

In a further object is a method for analyzing a compound with an amino group in a sample containing at least a compound with amino group by means of mass spectrometry, comprising labeling said compound with an amino group in said sample by reacting said compound with an amino group with the carbamate compound represented by formula (1)

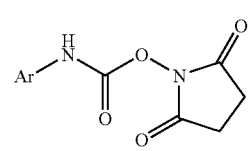

(1)

wherein Ar is a carbocyclic compound or a heterocyclic compound residue having an aromaticity where the aromatic ring may have one or more substituents, and wherein the bond between Ar group and a nitrogen atom in the carbamate group, the carbon atom constituting the ring in Ar group is bound to a nitrogen atom of the carbamate group, whereby the carbamate compound may be in a form of a salt, and subjecting the labeled compound to mass spectrometry.

In the aforementioned objects of the present invention, it is preferred that said mass spectrometry is tandem mass spectrometry. Tandem mass spectrometry methods include selected reaction monitoring method, a precursor ion scan method and a constant neutral loss scan method.

In yet another object of the present invention the aforementioned method is modified such that a sample containing a compound with an amino group labeled with a carbamate compound having one or more of stable isotope is mixed with another sample containing a compound with an amino group labeled with a carbamate compound having the same structure as the isotope-labeled carbamate compound which does not contain an isotopic label and analyzing the mixed sample by tandem mass spectrometry.

In the aforementioned objects, the amino compound includes amino acids, peptides, and proteins.

In still a further object of the present invention is carbamate compound selected from the group consisting of p-Dimethylaminoanilyl-N-hydroxysuccinimidyl carbamate, 3-aminopyridyl-N-hydroxysuccinimidyl carbamate, p-trimethylammonium anilyl-N-hydroxysuccinimidyl carbamate iodide, and aminopyrazyl-N-hyroxysuccinimidyl carbamate.

The above objects highlight certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily obtained as the same becomes better understood by reference to the following Figures in conjunction with the detailed description below.

This figure is an SRM chromatogram, which is obtained by an LC/MS/MS method of the labeled amino acids using p-trimethylammoniumaninyl-N-hydroxysuccinimidyl carbamate iodide (TAHS) as a labeling agent as described in Example 7 (Analytical Example 1). The final labeled amino acid concentration: 0.2 nmol/mL. TIC: Total ion chromatogram.

Figure 2:
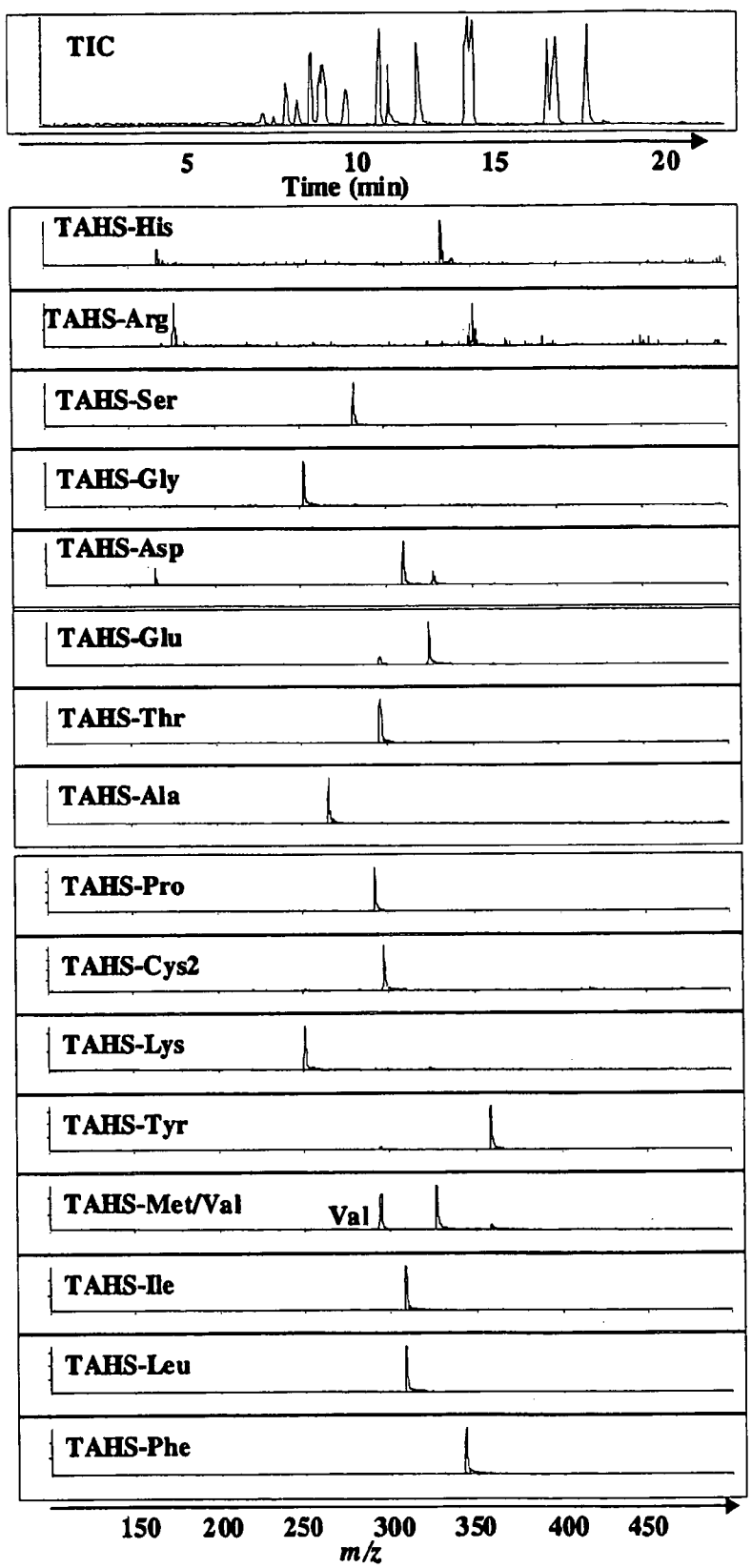

FIG. 2 shows the result of a precursor ion scan analysis of 17 TAHS-labeled amino acids.

This figure is a mass spectrum obtained by a precursor ion scan analysis of the labeled amino acids using p-trimethylammonium aninyl-N-hydroxysuccinimidyl carbamate iodide (TAHS) as a labeling agent as described in Example 8 (Analytical Example 2). The final labeled amino acid concentration: 2 nmol/mL. TIC: Total ion chromatogram.

Figure 3:
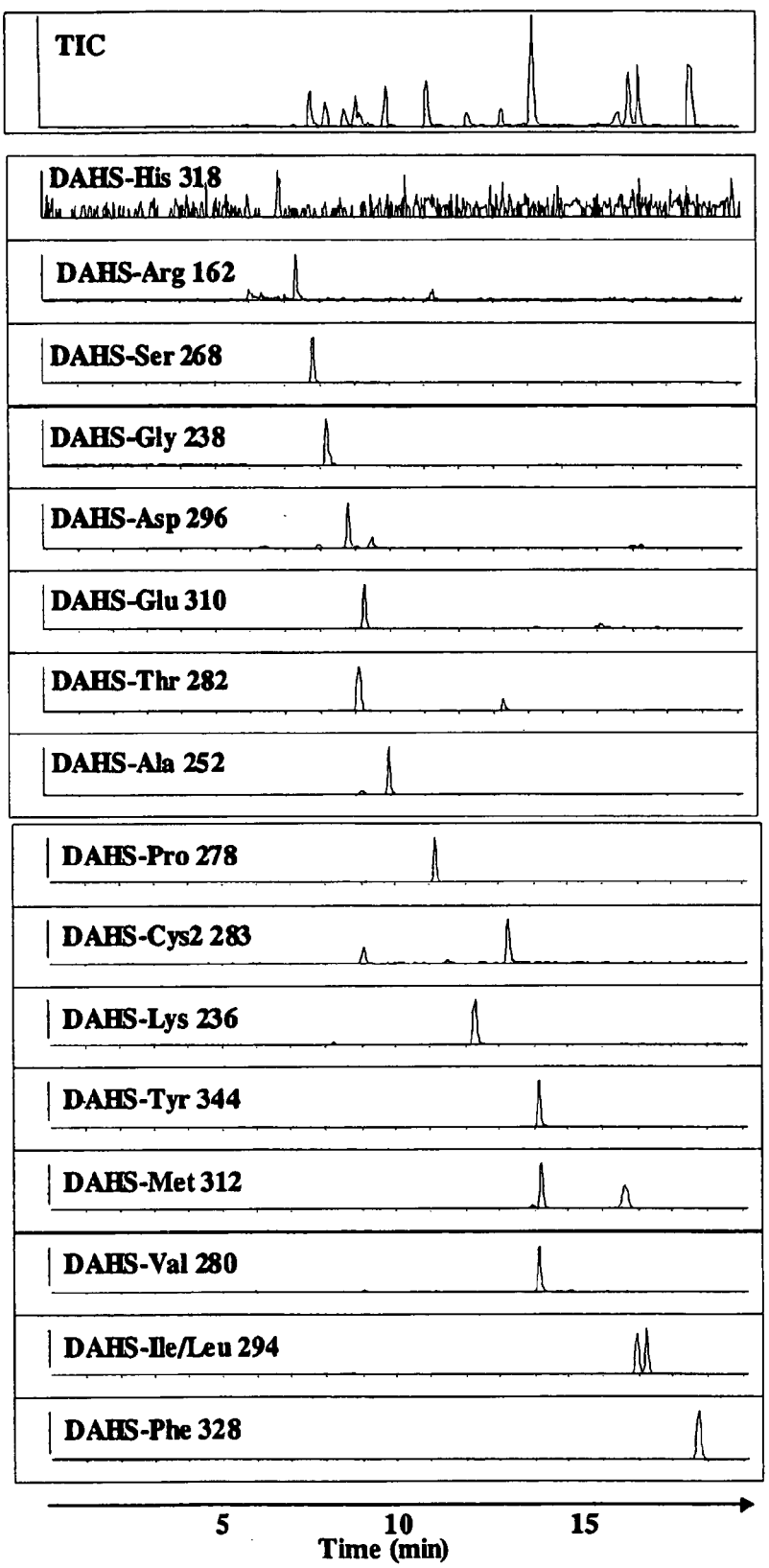

FIG. 3 shows the result of an SRM analysis of 17 DAHS-labeled amino acids.

This figure is an SRM chromatogram obtained by an LC/MS/MS method of the labeled amino acids using p-dimethylaminoaninyl-N-hydroxysuccinimidyl carbamate (DAHS) as a labeling agent as described in Example 9 (Analytical Example 3). The final labeled amino acid concentration: 0.2 nmol/mL. TIC: Total ion chromatogram.

Figure 4:
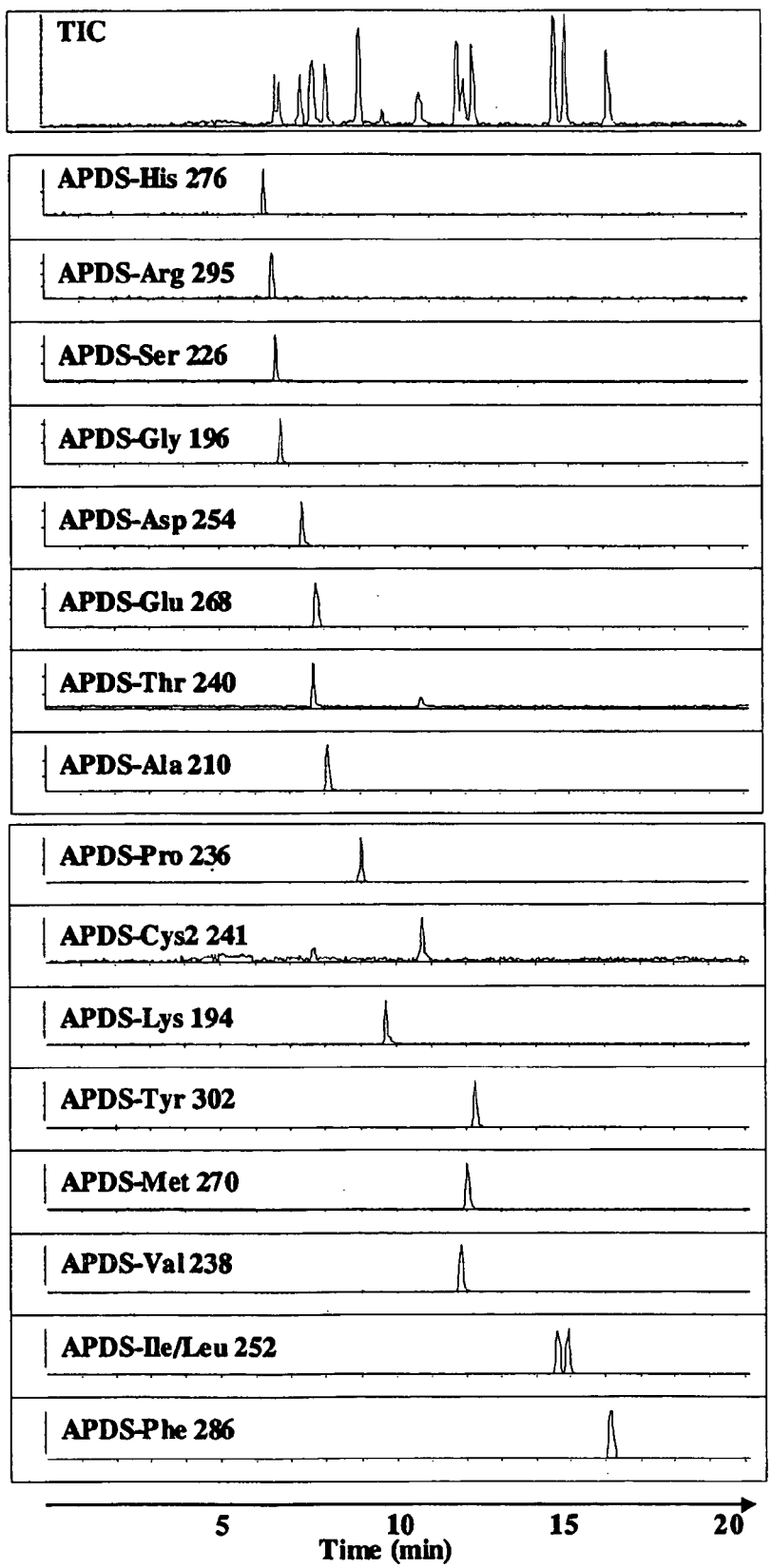

FIG. 4 shows the result of an SRM analysis of 17 APDS-labeled amino acids.

This figure is an SRM chromatogram obtained by an LC/MS/MS method of the labeled amino acids using 3-aminopyridyl carbamate (APDS) as a labeling agent as described in Example 10 (Analytical Example 4). The final labeled amino acid concentration: 0.2 nmol/mL. TIC: Total ion chromatogram.

Figure 5:
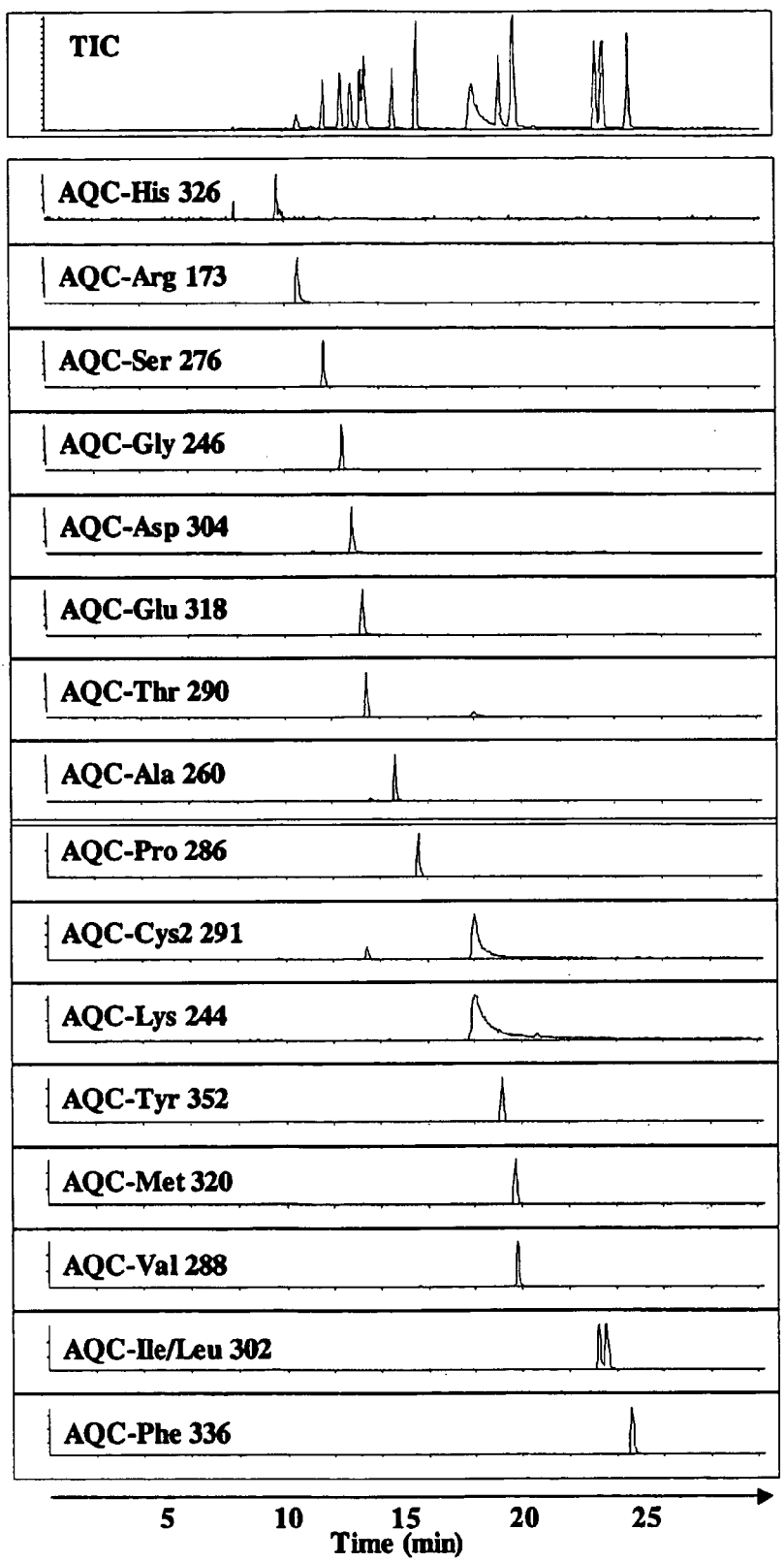

FIG. 5 shows the result of an SRM analysis of 17 AQC-labeled amino acids.

This figure is an SRM chromatogram obtained by an LC/MS/MS method of the labeled amino acids using 6-aminoquinolyl-N-hydroxysuccinimidyl carbamate (AQC) as a labeling agent as described in Example 11 (Analytical Example 5). The final labeled amino acid concentration: 0.2 nmol/mL. TIC: Total ion chromatogram.

Figure 6:
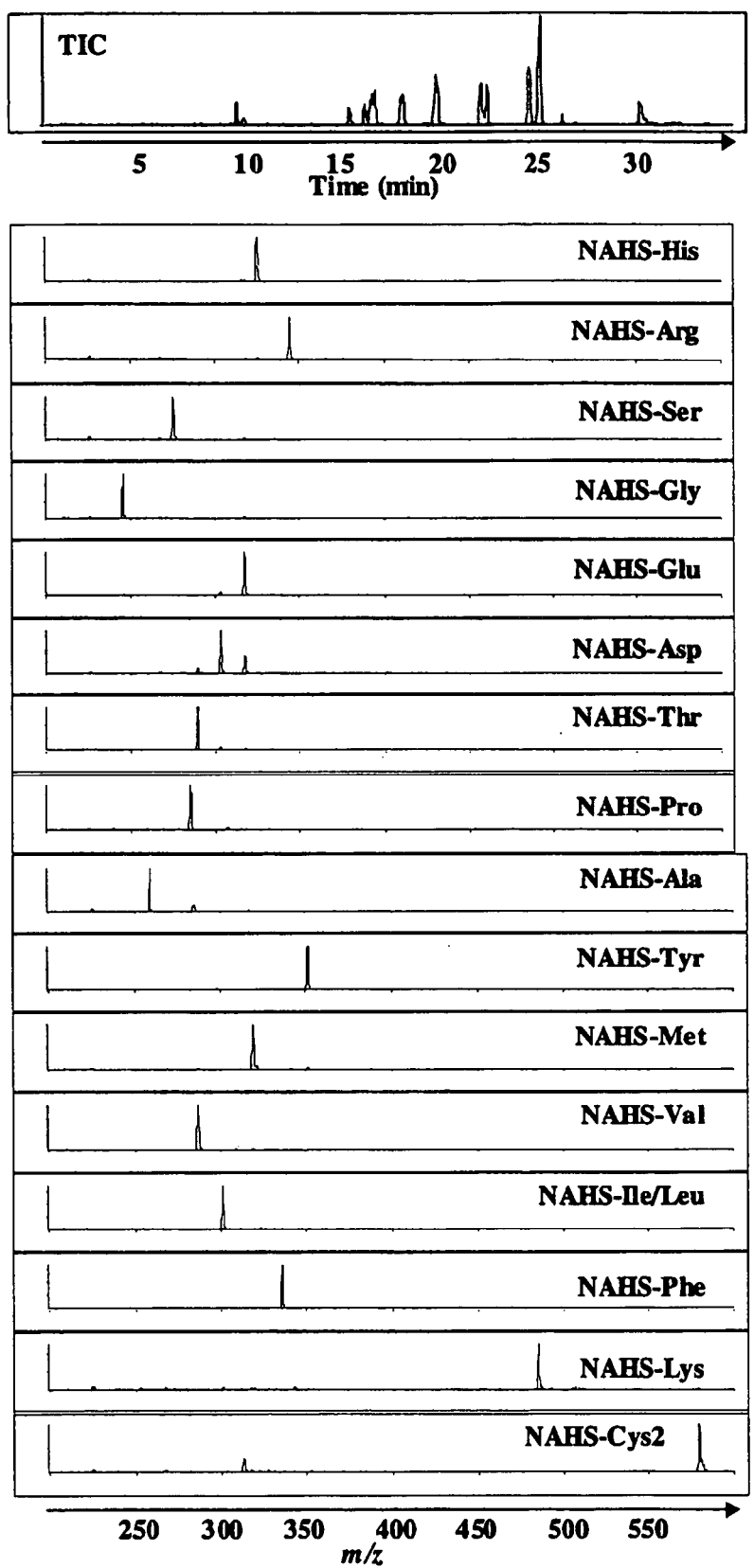

FIG. 6 shows the result of a constant neutral loss scan analysis of 17 NAHS-labeled amino acids.

This figure is a mass spectrum obtained by a constant neutral loss scan analysis of the labeled amino acids using 1-naphthylamino-N-hydroxysuccinimidyl carbamate (NAHS) as a labeling agent as described in Example 12 (Analytical Example 6). The final labeled amino acid concentration: 2 nmol/mL. TIC: Total ion chromatogram.

Figure 7:
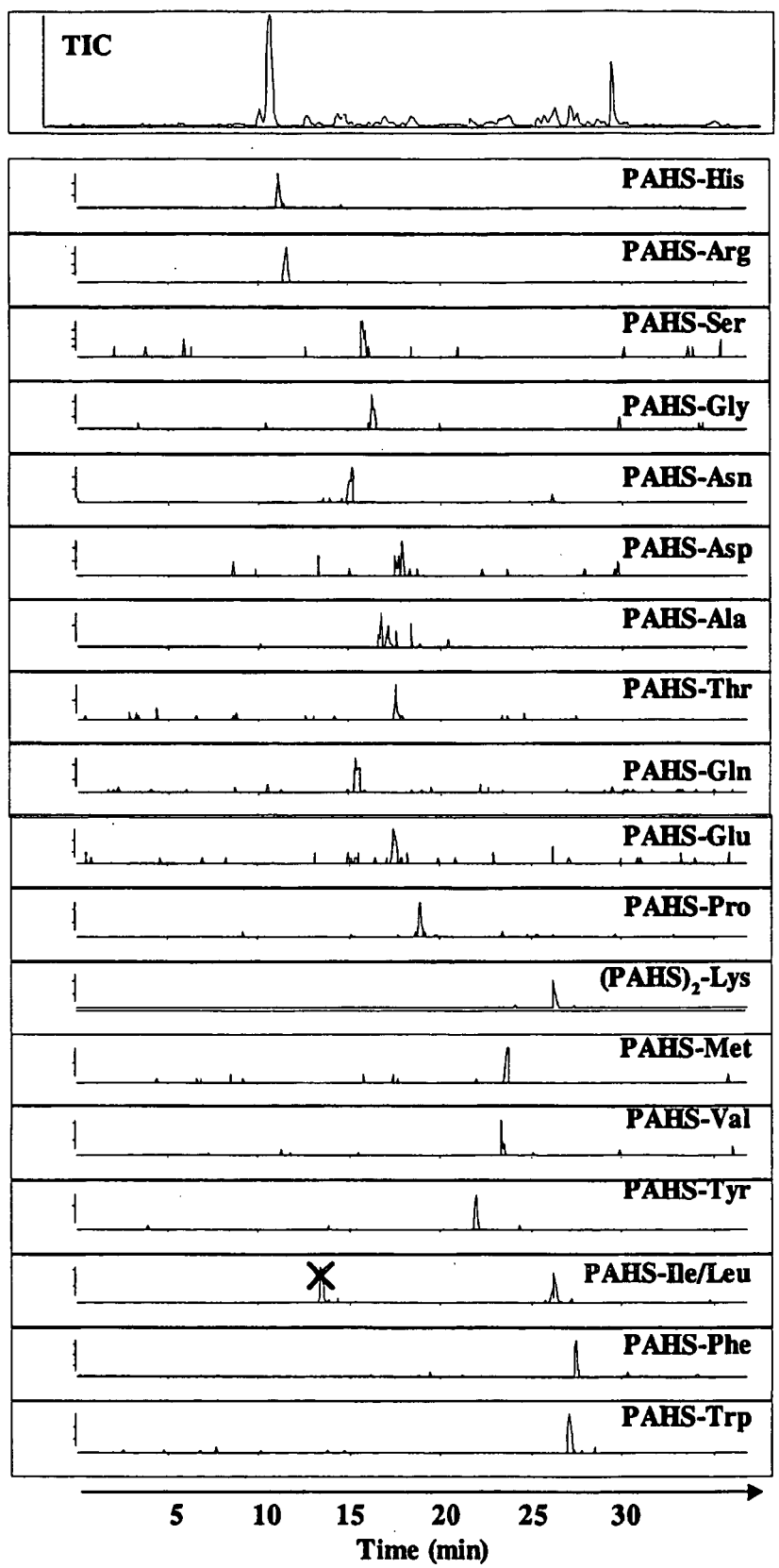

FIG. 7 shows the result of a constant neutral loss ion scan analysis of 19 PAHS-labeled amino acids.

This figure is a mass spectrum obtained by a constant neutral loss scan analysis of the labeled amino acids using PAHS as a labeling agent obtained in Example 13 (Analytical Example 7). The final labeled amino acid concentration: 5 nmol/mL.

Figure 8:
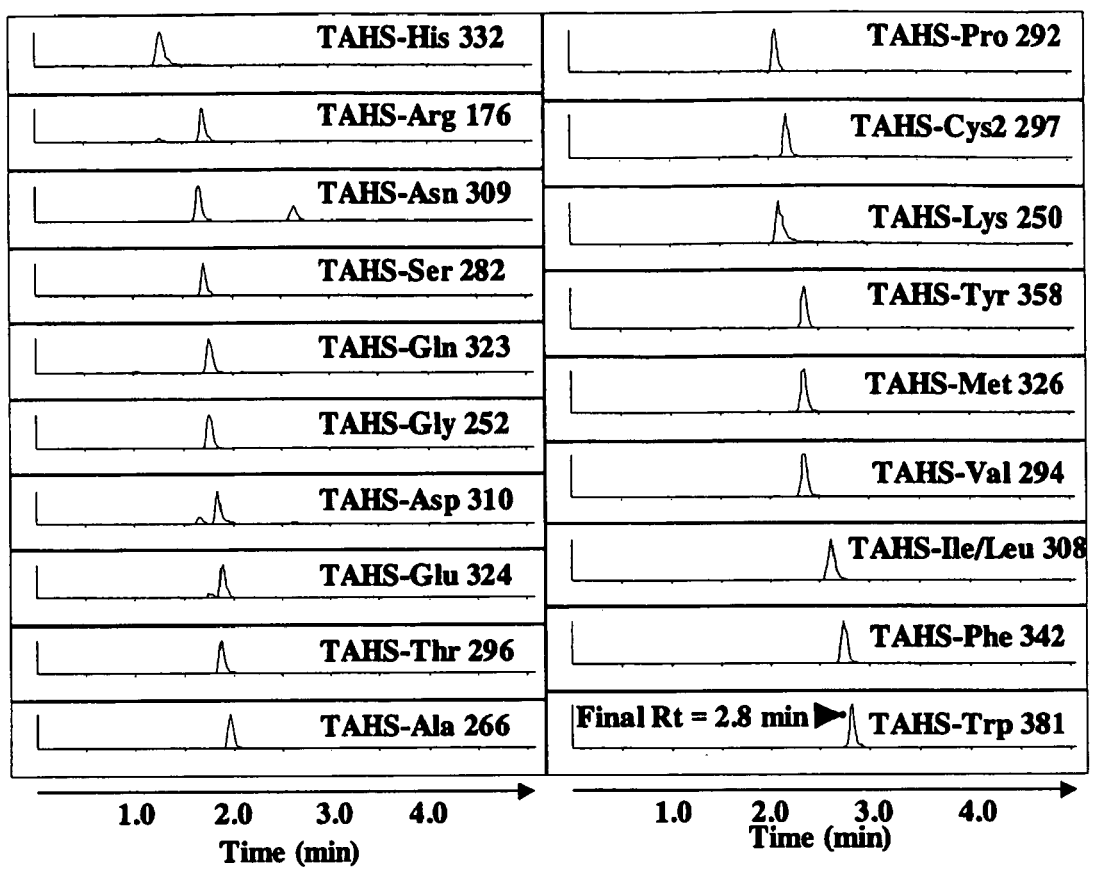

FIG. 8 shows an SRM chromatogram obtained by an LC/MS/MS method of the labeled amino acids using p-trimethylammoniumaninyl-N-hydroxysuccinimidyl carbamate iodide (TAHS) as a labeling agent as described in Example 14 (Analytical Example 8) (a high-performance analysis chromatogram of 20 kinds of amino acids). The final labeled amino acid concentration: 0.5 nmol/mL.

Figure 9:
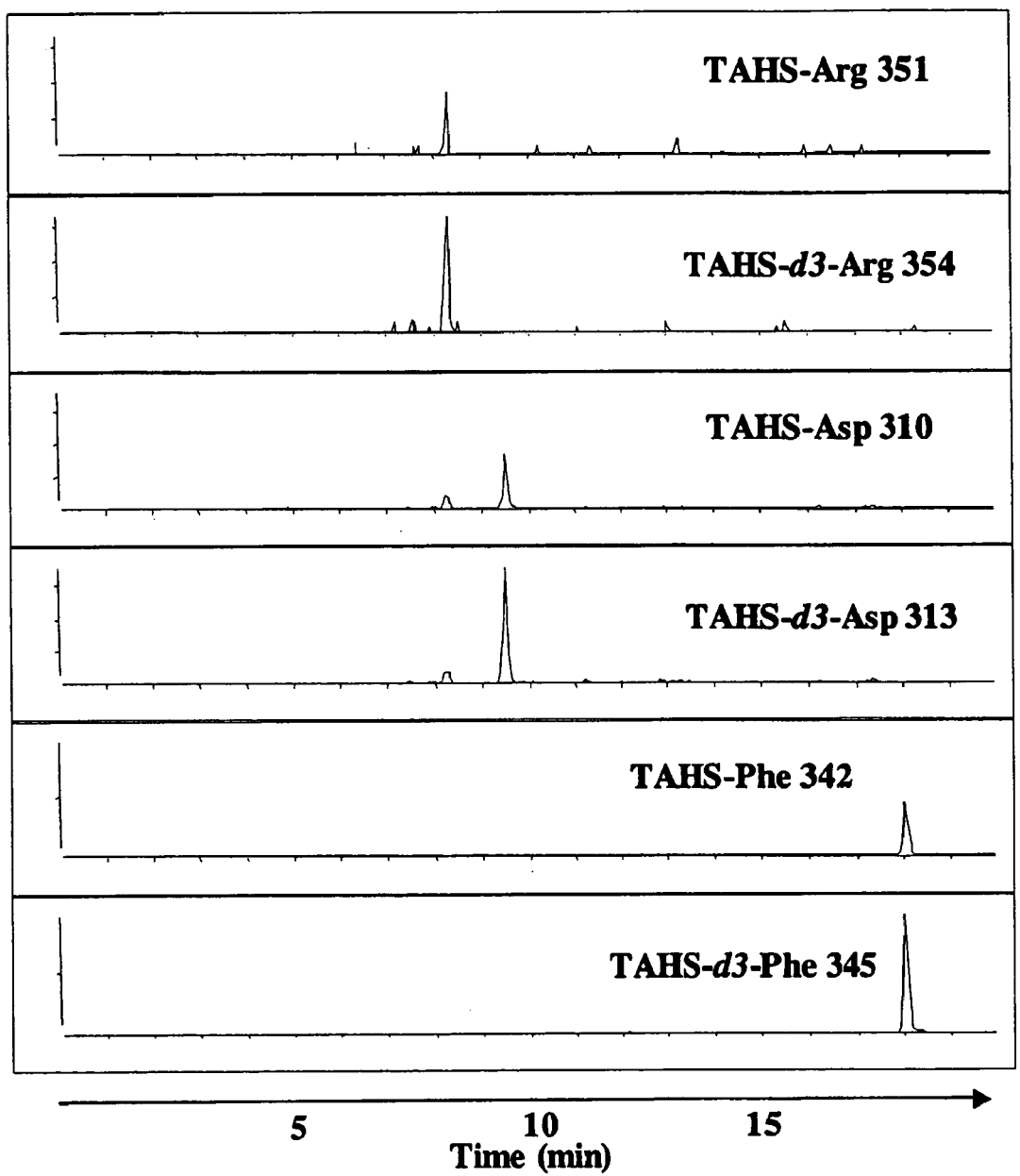

FIG. 9 shows an SRM chromatogram obtained by an LC/MS/MS method where two samples were measured at the same time for the amino acids using p-trimethylammoniumanilyl-N-hydroxysuccinimidyl carbamate iodide (TAHS) and p-trimethylammoniumaninyl-N-hydroxysuccinimidyl carbamate iodide-d3 (TAHS-d3) as labeling agents as described in Example 19 (Analytical Example 9).

Figure 10:
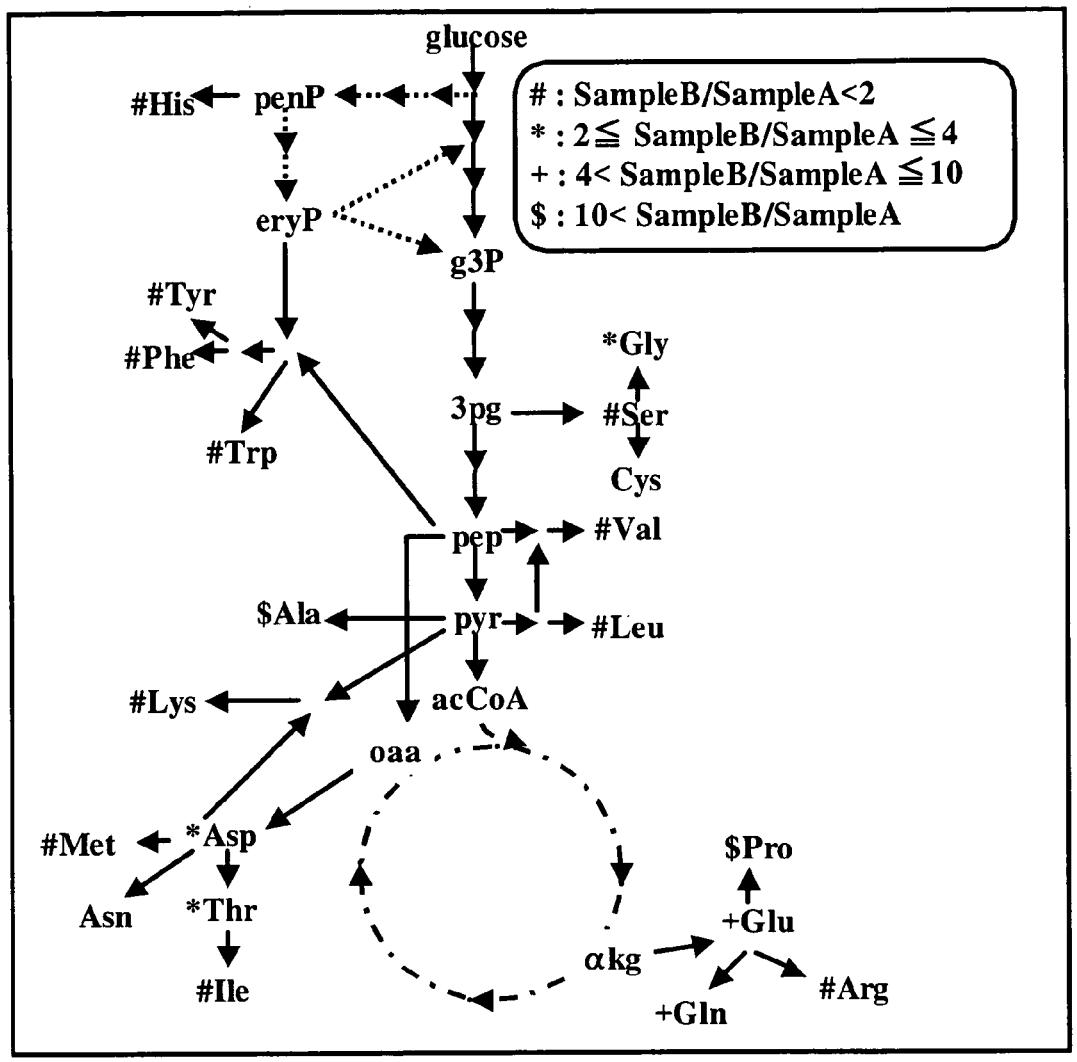

FIG. 10 is a reproduction, on a metabolism map, of a peak area ratio obtained by a simultaneous measurement by an LC/MS/MS method of amino acids in different two samples (sample A and sample B) using p-trimethylammoniumanilyl-N-hydroxysuccinimidyl carbamate iodide (TAHS) and p-trimethylammoniumaninyl-N-hydroxysuccinimidyl carbamate iodide-d3 (TAHS-d3) as labeling agents as described Example 20 (Analytical Example 10).

: (sample B)/(sample A)<2;
*: 2≦(sample B)/(sample A)≦4;
+: 4<(sample B)/(sample A)≦10; and
$: 10<(sample B)/(sample A).

DETAILED DESCRIPTION OF THE INVENTION

Unless specifically defined, all technical and scientific terms used herein have the same meaning as commonly understood by a skilled artisan in agriculture, enzymology, biochemistry, cellular biology, clinical chemistry, molecular biology, the medical sciences, and the pharmaceutical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The present inventors have conducted intensive studies for solving the problems that, heretofore, exist in the art and found that when a compound with an amino group (e.g., an amino acid and others) is labeled with a labeling reagent having a specific, defined structure and then the labeled compound is subjected to mass spectrometry (preferably, tandem mass spectrometry (MS/MS method)), it is possible to readily analyze the compound. In this regard, the identity of the amino group may be conveniently and selectively ascertained with a high sensitivity. As such, the present invention lies in methods of performing the same.

Thus, the present invention relates to a method for the analysis of a compound with amino group in a sample by means of mass spectrometry. The invention method for the analysis of a compound with amino group, etc. is characterized in that the compound is labeled with a carbamate compound represented by the following formula (1) and subjected to mass spectrometry. As sometimes denoted herein, this method is referred to as "the analytical method of the present invention."

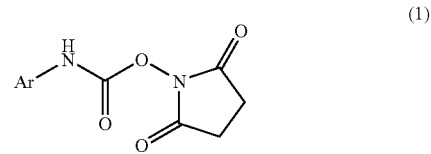

(1)

In the formula (1), Ar is a carbocyclic compound or a heterocyclic compound residue having an aromaticity where the aromatic ring may have (one or more) substituent(s) and, in the bond between Ar group and a nitrogen atom in the carbamate group, the carbon atom constituting the ring in Ar group is bound to a nitrogen atom of the carbamate group, whereby the carbamate compound may be in a form of a salt. The aromatic ring may be anything so far as it shares π electrons on the ring. In regard to the atoms constituting the ring, only carbon atoms (carbocyclic) or one or more carbon atoms and one or more atoms other atom than a carbon atom (preferably, nitrogen atom or sulfur atom) may be listed. It is possible to form the ring only by carbon atoms (carbocyclic) or by carbon and other atom (heterocyclic).

In the present invention, "compound with amino group" is used to designate a compound (which may be in a form of a salt) having one or more amino groups and/or one or more imino groups in the molecule and. The compound with an amino group in a sample may be one type or a mixture of a plurality of types.

In regard to Ar in formula (1), examples of a carbocyclic compound residues include: phenyl group, naphthyl group (1- and 2-naphthyl groups) and anthryl group (1-, 2- and 5-anthryl groups), each of which may be substituted. Examples of a heterocyclic compound residues include: pyridyl group (2-, 3- and 4-pyridyl groups), pyrazyl group, quinolyl group (2- to 8-quinolyl groups), acridyl group (1- to 4- and 9-acridyl groups) and coumaryl group (5- to 8-coumaryl groups), each of which may be substituted. In these groups, one or more substituent(s) may be present in the aromatic ring. Examples of the substituents include an alkyl group having 1 to 5 carbon(s), an aromatic group such as naphthyl group and phenyl group, a halogen atom such as chlorine atom, bromine atom, fluorine atom and iodine atom, carboxyl group, hydroxyl group, nitro group, diazo group, cyano group, an alkoxy group having 1 to 5 carbon(s), an acyl group having 2 to 7 carbons (such as acetyl group and benzoyl group), sulfonic acid group, phosphoric acid group, guanidyl group, dialkylamino group and trialkylammonium group. In order to detect the compound with an amino group with a high sensitivity, the compound is particularly preferred to have polar substituent(s), especially those that are apt to be ionized in a solvent. Examples of suitable polar substituents include: sulfonic acid group, phosphoric acid group, guanidyl group, dialkylamino group and trialkylammonium group.

Specific examples of Ar include the following groups: phenyl group, naphthyl group (1- and 2-naphthyl groups), anthryl group (1-, 2- and 5-anthryl groups), pyridyl group (2-, 3- and 4-pyridyl groups), pyrazyl group, quinolyl group (3-, 6- and 8-quinolyl groups), 9-acridyl group, 6-coumaryl group, p-dialkylaminophenyl group, p-trialkylammoniumphenyl group, 1-(3-trialkylammonium)naphthyl group, 1-(5-trialkylammonium)naphthyl group, 1-(3-dialkylamino)naphthyl group, 1-(5-dialkylamino)naphthyl group, p-sulfophenyl group, 1-(3-sulfo)naphthyl group, 1-(5-sulfo)naphthyl group, p-phosphophenyl group, 1-(3-phospho)naphthyl group, 1-(5-phospho)naphthyl group, p-guanidinophenyl group, 1-(3-guanidino)naphthyl group, 1-(5-guanidino)naphthyl group, etc.

Each alkyl group in the above-mentioned dialkylamino group and trialkylammonium group may independently be an alkyl group having 1 to 5 carbon atom(s).

Examples of the compound with amino group include amines (such as primary amine and secondary amine), amino acid, peptide and protein. Also within the scope of the present invention are compounds that possess plurality of amino groups or types of amino groups. Examples of compounds possessing a plurality of types of amino groups include amino acids, a mixture of one or more amino acid(s) with one or more peptide(s) and a mixture of one or more amino acid(s) with one or more amine(s).

In regard to mass spectrometry suitable for use in the present invention, there is no particular limitation so far as it is an analytical method utilizing analysis of mass. In a preferred embodiment, the detection method is tandem mass spectrometry (MS/MS method).

Representative examples of the MS/MS method are a selected reaction monitoring method, a precursor ion scan method and a constant neutral loss scan method. Methods which will be developed in future may be adopted as well so far as they are analytical methods within a scope of an MS/MS method.

When analysis is conducted for a sample containing plural types of compounds with amino groups, the total amount of the compounds with amino group may be quantified or they may be quantified for each compound. For example, in the case of analysis of a mixture of plural kinds of amino acids, total amino acids may be quantified or each amino acid may be quantified.

In one embodiment of the present invention is a method for the labeling of a compound with amino group suitable for mass spectrometry by reacting a compound having an amino group with a carbamate compound represented by the following formula (1) (labeling method).

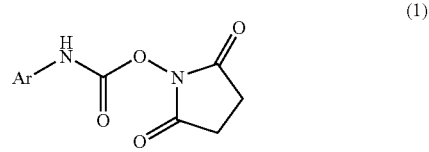

(1)

In the above formula, Ar is a carbocyclic compound or heterocyclic compound residue having an aromaticity, the aromatic ring may have one or more substituent(s) and, in the bond between Ar group and a nitrogen atom in the carbamate group, the carbon atom constituting the ring in Ar group is bound to a nitrogen atom of the carbamate group, whereby the carbamate compound may be in a form of a salt.

In another embodiment of the present invention is a reagent for the labeling of a compound with amino group, wherein the reagent is suitable for mass spectrometry and the reagent contains a carbamate compound represented by the following formula (1) (labeling reagent; labeling agent).

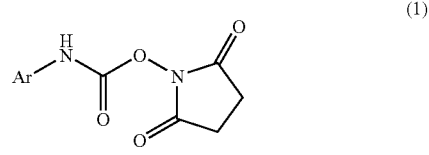

(1)

In the above formula, Ar is a carbocyclic compound or heterocyclic compound residue having an aromaticity, the aromatic ring may have one or more substituent(s) and, in the bond between Ar group and a nitrogen atom in the carbamate group, the carbon atom consitutting the aromatic ring in Ar group is bound to a nitrogen atom of the carbamate group, whereby the carbamate compound may be in a form of a salt.

In the embodiments above, scope and content of the compound with amino group and the carbamate compound are the same as those illustrated in the already-mentioned for the analytical method above.

A further embodiment of the present invention is a carbamate compound having the following formula (1) (novel compound) or a labeling reagent suitable for the analysis of a compound with amino group which is characterized in containing the carbamate compound (labeling agent).

That invention relates to a novel compound that can be used as a labeling reagent or to a labeling reagent containing the novel compound. Accordingly, in regard to the scope of the carbamate compound, the illustration for the carbamate compound mentioned above in relation to the already-mentioned analytical method of the present invention; however, already-known compounds are excluded by proviso (e.g., AQC known in the art as 3, 5, or 6-aminoquinolyl-N-hydroxysuccinimidyl carbamate (see U.S. Pat. No. 5,296,599)).

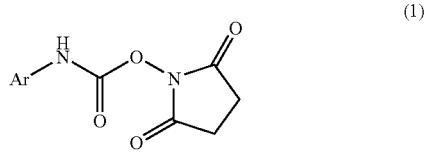
(1)

In the formula (1) above, Ar is preferably a carbocyclic compound or heterocyclic compound residue having an aromaticity where a polar substituent is bound to a ring or a pyridyl group or pyrazyl group where a polar substituent is not bound to the ring and, in the bond between Ar and a nitrogen atom in the carbamate group, the carbon atom constituting the ring in Ar may be bound to a nitrogen atom of the carbamate group, whereby the carbamate compound may be in a form of a salt.

In regard to pyridyl group and pyrazyl group, both may or may not have a polar substituent on an aromatic ring.

In the context of the present invention, Ar may be a quinolyl group where a polar substituent is not bound to the ring, with the proviso that the carbon atom at the 3, 5, or 6-position of said quinolyl group is not bound to a nitrogen atom of a carbamate group.

In the formula, examples of the carbocyclic compound or heterocyclic compound residue include phenyl group, naphthyl group (1- and 2-naphthyl groups), anthryl group (1-, 2- and 5-anthryl groups), pyridyl group (2-, 3- and 4-pyridyl groups), pyrazyl group, quinolyl group (3-, 6- and 8-quinolyl groups), acridyl group (1- to 4- and 9-acridyl groups) and coumaryl group (5- to 8-coumaryl groups). Examples of the above polar substituent are sulfonic acid group (—SO$_3$H, —SO$_3$Na, etc.), phosphoric acid group, guanidyl group, dialkylamino group and trialkylammonium group.

More preferred examples of Ar in the formula include 3-pyridyl group, pyrazyl group, p-dialkylaminophenyl group, p-trialkylammoniumphenyl group, 1-(3-trialkylammonium)naphthyl group, 1-(5-trialkylammonium)naphthyl group, 1-(3-dialkylamino)naphthyl group, 1-(5-dialkylamino)naphthyl group, p-sulfophenyl group, 1-(3-sulfo) naphthyl group, 1-(5-sulfo)naphthyl group, p-phosphophenyl group, 1-(3-phospho)naphthyl group, 1-(5-phospho) naphthyl group, p-guanidinophenyl group, 1-(3-guanidino) naphthyl group and 1-(5-guanidino)naphthyl group.

Each alkyl group in the above-mentioned dialkylamino group and trialkylammonium group may independently be an alkyl group having 1 to 5 carbon(s).

There is no particular difficulty in the labeling of the amino group (or imino group) of the compound with amino group used in the present invention by a labeling reagent (carbamate compound). The labeling is conducted by the reaction of the compound with amino group with the above carbamate compound. With regard to the condition for the labeling reaction, a general condition in the case of labeling using such a reagent (cf. Iwaki, K., Yoshida, S., Nimura, N., Kinoshita, T., Takeda, K., and Ogura, H., *Chromatographia*, 23, 899 (1987)) may be used. Preferably, a condition such as that a compound with amino group is mixed with a reagent and a labeling reagent dissolved in an appropriate organic solvent, except alcohol, under an environment of pH of about 8 to 10 and heated at about 60° C. may be used. In regard to the amount of the labeling reagent (carbamate compound) used, about 10- to 1000-fold mol (equivalents) or, preferably, about 100- to 1000-fold mol (equivalents) to the compound with amino group are used by taking the amount of the compound with amino group or, particularly, the amount of total amino group and imino group contained therein into consideration whereby all amino and imino groups are labeled.

There is no particular limitation for the preparation of the compound according to the present invention. An example of a method for the preparation thereof, the compound can be readily synthesized from an aromatic amine and N,N-disuccinimidyl according to the following reaction formula. In the case of the manufacture of a trialkylammonium salt, the compound of the present invention can be readily synthesized from its dialkylamine substance with alkyl iodide such as methyl iodide.

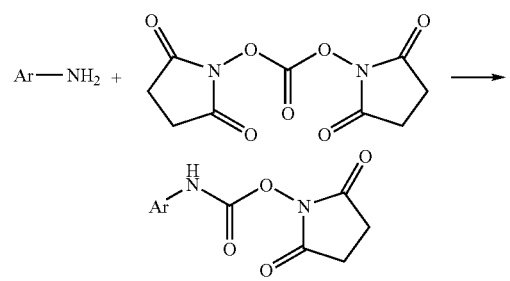

In the aforementioned illustration, Ar has the same meaning as Ar defined above in the analytical method of the present invention.

Novel compound of the present invention include the followings: p-Dimethylaminoanilyl-N-hydroxysuccinimidyl carbamate; 3-aminopyridyl-N-hydroxysuccinimidyl carbamate; p-trimethylammonium anilyl-N-hydroxysuccinimidyl carbamate iodide; and aminopyrazyl-N-hyroxysuccinimidyl carbamate.

All of the carbamate compound (novel compound) of the present invention and the carbamate compound used in the present invention may be in a free or a salt form. There is no particular limitation for the form of a salt. A desired salt may be prepared by utilizing a salt-preparing step which is used for the preparation of a salt of various amines. Examples include salts with an inorganic acid such as hydrochloric acid, sulfuric acid and nitric acid and with an organic acid such as acetic acid. A desired salt may be further prepared by using a reagent which is made to react with an amine for preparing a quaternary ammonium such as alkyl iodide (e.g., methyl iodide), alkyl bromide (e.g., methyl bromide) and alkyl chloride (e.g., methyl chloride). When there is an acidic substituent such as sulfonic acid group and phosphoric acid group, a derivative which is in a form of being neutralized with a basic substance, etc. is also included within such a salt.

As hereunder, embodiments of the present invention will be illustrated. The illustration will be done centering on the preferred representative examples and, therefore, the present invention is not limited thereto.

Principle of the Analytical Method

Mass spectrometry is used as an analytical method in the present invention and is illustrated by the following.

A compound with amino group such as amino acid may be labeled with a labeling reagent according to the following reaction formulae.

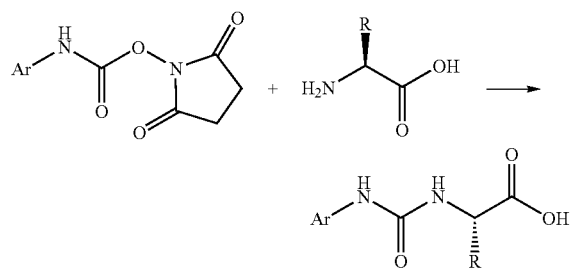

Ar has the same meaning as Ar defined in the above analytical method of the present invention. R in the above formula showing an amino acid is an appropriate substituent whereby the formula represents various amino acids. When R further contains amino group or imino group as in the case of a basic amino acid, a carbamate compound reacts with such a group as well.

When a labeled substance with an amino acid for example with a labeling reagent which is the above-mentioned carbamate compound is subjected to a collision-induced dissociation (CID) in a mass spectrometer, a selective cleavage results at the site as shown by a dotted arrow in the following reaction formulae. In regard to a labeling reagent, when a substance where the above-mentioned dialkylamino group or trialkylammonium group as a substituent for example is preferably bonded to a carbocyclic or a heterocyclic is selected for enhancing a cationic property and when a setting is made so as to observe positive ion by a mass spectrometer, then a structure derived from amino acid results in a neutral loss and only a fragment ion [Ar—NH—CO] derived from the reagent is selectively detected.

When the above is utilized and the following two kinds of measuring methods, i.e., a precursor ion scan method and a selected reaction monitoring method (SRM method), are performed, ion of a reaction product of the compound with amino group with the above labeling reagent and fragment ion derived from the reagent are detected by the first and the second mass analyzers, respectively, whereupon a very highly selective and a highly sensitive analysis is able to be achieved. Ar has the same meaning as the above-mentioned Ar.

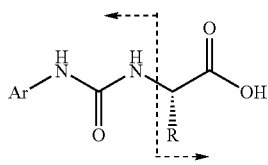

Such a characteristic feature has been noted in p-dimethylaminoanilyl-N-hydroxysuccinimidyl carbamate (DAHS), 3-aminopyridyl-N-hydroxysuccinimidyl carbamate (APDS), p-trimethylammoniumanilyl-N-hydroxysuccinimidyl carbamate iodide (TAHS), aminopyrazyl-N-hydroxysuccinimidyl carbamate, 6-aminoquinolyl-N-hydroxysuccinimidyl carbamate (AQC), 9-aminoacridyl-N-hydroxysuccinimide carbamate, etc.

On the other hand, when a compound where ionic property of the reagent is small is selected from the above carbamate compounds as a labeling reagent, although a selective cleavage is generated in the site shown by a dotted arrow by a CID in the same manner, the structure derived from the reagent results in a neutral loss when a setting is done in such as manner that positive ion is observed in a mass spectrometer whereupon [amino acid+H] is observed as a fragment ion. When that is utilized and a setting is done in such a manner that positive ion is observed by a mass spectrometer by means of a constant neutral loss scan method and then ion of the reaction product of amino acid with reagent and ion derived from amino acid where the structure derived from the reagent results in a neutral loss are detected by the first and the second mass analyzers, respectively, whereupon a very highly selective and highly sensitive amino acid analysis is achieved. Such a characteristic feature has been shown by 1-naphthylamino-N-hydroxysuccinimidyl carbamate (NAHS).

Suitable Mass Spectrometry

Although there is no particular limitation for the mass spectrometry used in the present invention, several ones will be introduced hereunder as more preferred examples.

Precursor Ion Scan

In a precursor ion scan analysis, the first mass analyzer (such as Q1) scans over the appropriate mass range and ions within the range are dissociated by a CID in, for example, Q2. In that case, the second mass analyzer (such as Q3) is set in such a manner that a specific fragment ion (such as $m/z=177$ in the case of TAHS) is selected. In the resulting spectrum, only a precursor ion (parent ion) which produces a specific fragment ion is recorded.

Selected Reaction Monitoring (SRM)

In an SRM analysis, the target ion is selected by the first mass analyzer (such as Q1) and this ion is dissociated in a collision cell and, in the second mass analyzer (such as Q3), a specific fragment ion (such as $m/z=177$ in the case of TAHS) is selected and monitored. According to this method, even when contaminant component having the same retention time with the compound to be quantified and the same mass as the precursor ion is present, its influence can be eliminated unless the contaminant component produces a fragment ion of the compound to be quantified. Thus, as a result, both sensitivity and selectivity are significantly improved.

Constant Neutral Loss Scan

In a constant neutral loss scan analysis, the first mass analyzer (such as Q1) is scanned according to the designated mass range and the ion within such a range is dissociated by a CID in, for example, Q2. In that case, the second mass analyzer (such as Q3) is set in such a manner that a specific neutral fragment (such as $m/z=170$ in the case of 1-naphthylamino-N-hydroxysuccinimidyl carbonate) is selected. In the resulting spectrum, a scanning method where all precursor ions (parent ions) dissociated by a specific neutral molecular are detected is adopted.

The mass spectrometry can detect an ion caused by the mass of the substance which is to be analyzed and, therefore, it has been widely used as a very highly selective detection method. In the present invention, a labeling reagent is designed where the substance to be analyzed generates regular cleavage whereby a detection method in which the compound with amino group is more highly selected has been achieved. Further, when a labeling reagent having a high ionic property is designed, a highly sensitive analysis of compound with amino group is able to be achieved.

Generally, in mass spectrometry, many impurities exist in the low-molecular region and they cause "noise." This noise is a factor for disturbing the detecting ability of the substance to be analyzed. However, when one or more aromatic ring(s) is/are introduced into a reagent, molecular weight is made large and a measurement in a region where the noise is minimized can be achieved.

Detection limit of amino acid varies depending upon the type of the amino acid and, when a quadrupole mass spectrometer such as a detector of an API 365 type (Applied Biosystems) is used and an SRM mode is selected, it is about 2 to 40 fmol in the case of p-trimethylammoniumanilyl-N-hydroxysuccinimidyl carbamate iodide (TAHS), about 3 to 2000 fmol in the case of p-dimethylaminoanilyl-N-hydroxysuccinimidyl carbamate (DAHS), about 3 to 180 fmol in the case of 3-aminopyridyl-N-hydroxysuccinimidyl carbamate (APDS) and about 2 to 200 fmol in the case of 6-aminoquinolyl-N-hydroxysuccinimide carbamate (AQC) whereupon it has been confirmed that the result is able to be better than common reagent for fluorescence labeling (refer to the Examples which will be mentioned later). Particularly, 6-aminoquinolyl-N-hydroxysuccinimide carbamate (AQC) has been put into the market as a reagent for fluorescence labeling and its detection limit has been reported to be several hundred fmol. In the measurement by means of an SRM, the sensitivity is noted to be from similar to that in a fluorescence method to 100-fold improvement at the highest.

Improvement in the mass spectrometric apparatus has been briskly performed by companies for the apparatus (such as Applied Biosystems). In the measurement using the latest quadrupole mass spectrometer (such as API 4000 (Applied Biosystems)), the detection limit for amino acid after being labeled with 6-aminoquinolyl-N-hydroxysuccinimide carbamate is not more than 1 fmol in most of amino acids (refer to the Examples which will be mentioned later).

The detection method of the present invention is conducted by an ion which is related to mass of the labeled compound with amino group and, therefore, there is no disturbance by other compounds, for example, the labeling reagent, hydrolysate of the labeling reagent and others such as unexpected impurities formed by the labeling reaction whereupon the substance to be analyzed is able to be measured.

In the precursor ion scan and the neutral loss scan, all of the labeled compounds with amino group are able to be detected. Therefore, when a non-identified compound is detected, it is now possible to estimate its structure from measured mass number, etc. by a mass spectrum.

General Methods for Carrying out the Invention

Now, general methods for carrying out the present invention will be illustrated. In regard to a compound with amino group in a sample, a mixed solution of amino acids is used.

Labeling of a compound with amino group by a carbamate compound having an aromatic amine is usually prepared as follows. For example, a borate buffer (0.2M of a borate and 5 mM of EDTA) or other buffer having pH 8 to 9.5 (such as phosphoric acid, etc. as an acidic salt while NaOH, $Na_2CO_3$, etc. as a basic salt) is added to a standard amine solution. Taking the solubility of the labeling reagent in an organic solvent into consideration, it is also possible to add the above-mentioned borate buffer or a mixture of the buffer with a non-alcoholic organic solvent such as acetonitrile.

A reagent solution (3 mg of a carbamate compound in 1 mL of acetonitrile of an HPLC grade) is added to the mixture. The resulting mixture is heated, for example, at 55° C. for 10 minutes.

A labeled amino acid (compound with amino group) prepared as such is separated using a reversed phase column and then introduced into a mass spectrometer. General conditions are as follows.

a) HPLC: Agilent HP 1100;

b) Column: Develosil C30 UG 5 μm, 4.6 mm I. D.×250 mm;

c) Detector: Mass spectrometer Sciex API 365;

d) Mobile phase

Mobile phase A: 0.2% AcOH

Mobile phase B: 0.2% AcOH in $CH_3CN$

Gradient: 0 min: 0%→20 min: 30%; and e) Temperature: 40° C.

When a labeled amino acid is detected in an SRM mode, the mass which is a labeled substance of a designated amino acid is selected by the first mass analyzer (such as Q1) in an MS/MS method in a positive ion mode of a mass spectrometer while a fragment ion of the reagent is selected by the second mass analyzer (such as Q3) whereupon the measurement is conducted.

Thus, when there is one amino group or imino group present in a molecule (compound with amino group) is taken as an example, mass [(amino acid+labeled reagent−HOSu+H) or (amino acid+labeled reagent-HOSu) in the case of a quaternary ammonium reagent] which is a labeled substance of an amino acid is selected by the first mass analyzer (such as Q1) while a fragment ion derived from the reagent is selected by the second mass analyzer (such as Q3) whereupon the measurement is conducted. "HOSu" means N-hydroxysuccinimide.

When only a labeled amino acid is detected by a precursor ion scan mode, in an MS/MS method in a positive ion mode of a mass spectrometer, the first mass analyzer (such as Q1) scans according to the already-set mass range while the second mass analyzer (such as Q3) selects and measures the mass of a specific fragment ion which was set already whereupon the measurement is conducted.

Thus, the set mass range (for example, m/z=100 to 600) is scanned by the first mass analyzer (such as Q1) while a fragment ion derived from the reagent is selected by the second mass analyzer (such as Q3) whereupon the measurement is conducted.

Only a labeled amino acid is detected by a constant neutral loss scan, in an MS/MS method in a positive ion mode of a mass spectrometer, the first mass analyzer (such as Q1) scans according to the set mass range while the second mass analyzer (such as Q3) measures all precursors giving a set specific neutral fragment.

Thus, the first mass analyzer (such as Q1) scans the set mass range (for example, m/z=100 to 600) while the second mass analyzer (such as Q3) selects a precursor ion where neutral fragment is lost (loss) derived from the reagent whereupon the measurement is conducted.

Synthetic Method for Labeled Reagent

An aimed labeling reagent can be readily prepared by a conventional method (refer, for example, to Iwaki, K., Yoshida, S., Nimura, N., Kinoshita, T., Takeda, K., and Ogura, H., *Chromatogrphia,* 23, 899 (1987)). For example, a carbamate compound represented by the following formula (1)

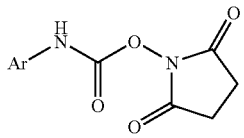

(1)

(in the formula, Ar has the same meaning as Ar above) can be synthesized by adding an aromatic amine compound in a non-alcoholic organic solvent such as acetonitrile into N,N-disuccinimidyl carbonate (DSC) using a dropping funnel when there is no trialkylammonium group in Ar. On the other hand, when a carbamate compound is prepared having a trialkylammonium group contained in the Ar group, a carbamate compound having a dialkylamino group is first prepared as mentioned above followed by treating with an alkyl iodide such as methyl iodide whereupon the product is synthesized.

Examples of the labeling reagent synthesized by the method above include: p-dimethylaminoanilyl-N-hydroxysuccinimidyl carbamate, 3-aminopyridyl-N-hydroxysuccinimidyl carbamate, p-trimethylammonium anilyl-N-hydroxysuccinimidyl carbamate iodide, naphthylamino-N-hydroxysuccinimidyl carbamate, aminopyrazyl-N-hydroxysuccinimidyl carbamate and 9-aminoacridyl-N-hydroxysuccinimide carbamate.

When the present invention is utilized, it is now possible to conduct analysis of a compound with amino group within a short period, measurement of isotope of a compound with amino group, presumption of structure of an unidentified compound, simultaneous measurement of plural samples, etc. and that will be illustrated to some extents as hereunder.

Analysis of a Compound With Amino Group Within a Short Period

In accordance with the present invention, it is possible to conduct analysis of a compound with amino group, particularly amino acid, within a short period. Analysis within a short period is now possible using a labeling reagent such as p-trimethylammoniumanilyl-N-hydroxysuccinimidyl carbamate iodide (TAHS). As a result, time for the analysis can be greatly shortened and, therefore, a treating ability is improved. For example, in the amino acid analysis using a conventional AQC reagent, the time for analysis is about 35 minutes (AccQ.Tag™ Amino Acid Analysis (Waters)) and time for analysis by the present invention is shorter.

Measurement of Isotope of a Compound With Amino Group

In the present invention, it is possible to measure an isotope of a compound with amino group and, as a result, it is now possible to determine the isotope ratio of the compound with amino group in a highly sensitive manner without calculation for the correction.

The method of the present invention is provided by utilizing a regular cleavage at the bonded site derived from the reagent with a compound with amino group by means of a collision-induced dissociation in a mass spectrometer.

Thus, in the present invention, it is possible to measure an isotope of a compound with amino group particularly by the use of a selected reaction monitoring method in the method of the present invention and, as a result, ratio of isotopes can be determined. In regard to the labeling reagent, there may be used a reagent where a compound with amino group such as amino acid is selectively cleaved thereby upon analysis and the fragment ion thereof is detected in a highly sensitive manner such as a labeling reagent of AQC and TAHS.

Prior Art Concerning the Measurement of Isotope

Analytical method utilizing an isotope composition which is different from that in nature has been used already. For example, a substrate containing a stable isotope having a low naturally existing rate such as $^{13}C$, $^2H$ (D), $^{15}N$ and $^{18}O$ or a radioactive isotope is introduced into a living body whereupon distribution or change of the substrate in the living body is checked has been used not only in medical and pharmaceutical fields but also in various fields of search. If the isotope is able to be evaluated quantitatively with a high sensitivity, it is possible to trace the behavior of the isotope atom and that leads to acquirement of further information. However, in measuring a compound with amino group by mass spectrometry in a direct manner, its sensitivity is a problem. On the other hand, when isotope ratio of a compound with amino group derivatized by a labeling reagent is analyzed by mass spectrometry in a high sensitivity, it is necessary to take the natural isotope distribution of the skeleton part other than the compound with amino group into consideration whereby it is necessary to correct the analytical result and to calculate the isotope ratio of the aimed compound.

For example, in a GC-MS (gas chromatography-mass spectrometry) method, conversion to a derivative the same as in the method of the present invention is conducted but, in most of the cases, a troublesome calculation for correction caused by natural isotope ratio distribution of the reagent part is necessary.

In addition, in an NMR method, sensitivity is low and a wide dynamic range is narrow and, therefore, it is not suitable for the detection of an isotope in small amount.

Content and Embodiment of the Present Invention

Attention is paid to the fact that regular cleavage at the positions of the amino group of the compound with amino group and of the carbonyl group of the reagent is particularly important. In a tandem mass spectrometer, a regular cleavage occurred at the bonded site derived from the compound with amino group and the reagent to give a fragment ion whereupon it is now possible to calculate the isotope ratio of the aimed compound with amino group without correction of the natural isotope distribution at the site corresponding to the reagent. In addition, when a mass spectrometer of a triple quadrupole type is used for example, a highly sensitive analysis of the isotope ratio in a broad dynamic range is possible.

In the present invention, in a tandem mass spectrometry/spectrometer, the mass spectrometry of the present invention is performed using, for example, a reagent by which the derivatized amino acid contained therein is selectively cleaved and the resulting fragment ion is detected in a high sensitivity whereupon the measurement of isotope of the aimed compound with amino group is able to be conducted and, as a result, the aimed isotope ratio can be determined.

Principle of the Analysis

In the present invention, a selected reaction monitoring method among the tandem mass spectrometry is adopted. Incidentally, the compound having a difference of one mass unit of isotope is quantified. Therefore, it is possible to conduct a measurement with a resolving power where one mass unit may be recognized.

Presumption of Structure of Unidentified Compound

When the labeling reagent of the present invention is used, then (1) those which are labeled are primary and secondary compounds with amino group;

(2) it is possible to determine a composition formula from a precise mass; and (3) it is now possible to narrow down the structure of an unidentified compound from the information of (1) and (2).

Thus, when the labeling reagent and the analytical method of the present invention are used, it is now possible to conduct a profiling method of a compound with amino group in a sample and to presume the structure of a target compound obtained by a profiling method. The labeling reagent of the present invention not only gives mass information with a high sensitivity but also gives a regular cleavage at the bonded site of the labeling reagent part with the compound with amino group. Therefore, since the information for the resulting fragment ion is identical with the fragment ion information of the unknown compound with amino group, it is now possible to carry out the structure analysis more easily.

Prior Art for Structure Analysis

With regard to an unknown peak appeared upon derivatizing by a reagent having ultraviolet absorption or fluorescence followed by analyzing, it was only possible to estimate the functional group of the compound from the reactivity with the reagent used for the derivatization. In addition, when an NMR is used, it often happens that analysis of a compound in a small amount is difficult in view of sensitivity.

When a mass spectrometer is used, mass information for an unknown compound obtained in a high sensitivity or information for fragment ion for an unknown compound is a useful information for conducting a structure analysis.

Carrying Out of the Method of the Present Invention

A specific peak or an aimed peak is found from a sample and a compound corresponding to the specific or aimed peak is identified or estimated for the structure thereof.

For example, in tandem mass spectrometry, it is possible to selectively monitor all of the compounds which regularly cleave between the part of the sample giving a derivative and a compound which is to be made into a derivative by the use of a precursor ion scan method or a constant neutral loss scan method. Thus, the compound with amino group reacted with a reagent giving a derivative is entirely detected and a specific peak or an aimed peak is found therefrom whereupon information concerning the mass is able to be obtained.

Further, in regard to the obtained peak, a precise mass is determined using an apparatus which is able to measure a precise mass whereupon a composition formula of the aimed compound is obtained and its structure is narrowed down from public databases or the like. It is also possible to estimate the structure of the aimed compound by conducting an analysis of fragment ion of the compound with amino group part obtained by a product ion scan method. For example, an unknown sample is labeled with NAHS (or PAHS), measurement by a constant neutral loss scan method is conducted and an aimed peak is selected. Here, it is possible to know the composition formula as structurally unknown compound with amino group which is derivatized when the precise mass is measured for the aimed peak. It is further possible by means of a product ion scan method to obtain a composition formula of the unknown compound per se from a precise mass of the compound with amino group obtained by a fragment ion. It is also possible to obtain a chemical formula of further fragment ion and, when a database is used together, it is still possible to narrow down the presumed structure.

Simultaneous Measurement of Plural Samples

In the present invention, the above-mentioned analytical method of the present invention is utilized and a compound having an isotope composition where all or a part of the atoms in the reagent are different from the natural one is used, it is now possible to measure plural samples at the same time.

Thus, as still another embodiment, the present invention relates to a carbamate compound represented by the following formula (1) which is a carbamate compound being characterized in containing a stable isotope element on at least one atom (excluding an exchangeable hydrogen atom) contained in the structure O=C—NH—Ar.

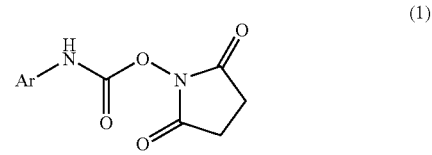

(1)

In the above formula, Ar is a carbocyclic compound or a heterocyclic compound having an aromaticity; the aromatic ring may have one or more substituent(s); and, with regard to the bond between Ar group and nitrogen atom of a carbamate group, a carbon atom constituting the ring in the Ar group is bound to a nitrogen atom of the carbamate group whereupon the carbamate compound may be in a form of a salt.

In the formula, Ar may be selected from optionally substituted phenyl group, naphthyl group, anthryl group, pyridyl group, pyrazyl group, quinolyl group, acridyl group and coumaryl group.

The substituent in case Ar is substituted may be selected from alkyl group, aromatic group, halogen atom, carboxyl group, hydroxyl group, nitro group, diazo group, cyano group, alkoxy group, acyl group, sulfonic acid group, phosphoric acid group, guanidyl group, dialkylamino group and trialkylammonium group.

In regard to the above-mentioned carbamate compound used in the present invention, that is the same as that illustrated for the carbamate compound used for the analytical method of the present invention.

A stable isotope contained in the above-mentioned carbamate compound may be selected from $^{13}C$, $^{2}H$ (D), $^{15}N$ and $^{18}O$.

As still another embodiment of the present invention is a sample which is made to react with a carbamate compound (labeling reagent) containing no stable isotope is mixed with a sample which is made to react with a carbamate compound (labeling reagent) having the same structure (same skeleton) as the above-mentioned carbamate compound and plural samples are analyzed at the same time using a tandem spectrometer.

In regard to the above carbamate compound containing no stable isotope, that which is not synthetically induced or that which follows the natural existing ratio may be adopted.

In regard to the carbamate compound having the same structure as the above carbamate compound, a compound containing $^{12}C$ and/or $^{13}C$ in a molecule may be adopted.

In this method, it is possible to include a method where the resulting analytical result is determined in a relative, semi-quantitative and visible manner or, particularly, a method where expression is made in such a manner that a relative comparison is possible.

In the above method, although a representative one is given, it is possible that, for plural samples, plural compounds which are carbamate compounds (labeling reagent) having the same structural skeleton and having different isotope composition each other are prepared, each sample is made to react with each carbamate compound and a mixture thereof as a single sample is subjected to a mass spectrometry of the present invention whereupon plural samples are measured at the same time.

For example, the present method provides a method wherein a sample which is reacted with a carbamate compound (labeling reagent) and another sample which contains one or more stable isotopes to the above one carbamate compound and is reacted with a carbamate compound (labeling reagent) having the same structure as the above-mentioned carbamate compound are mixed and the plural samples are analyzed at the same time using a tandem mass spectrometer; and a method wherein, to plural samples, plural kinds of carbamate compounds containing each different numbers of isotope and having the same structure (formula) with different mass are prepared, each sample is made to react with one kind of each of the carbamate compounds being different each other, then the reaction products of the samples are mixed and plural samples are analyzed at the same time using a tandem mass spectrometer.

In the aforementioned methods, it is possible to use a reagent by which reagent side is able to be detected by the second mass analyzer such as 6-aminoquinolyl-N-hydroxysuccinimidyl carbamate (AQC), p-trimethylammoniumanilyl-N-hydroxysuccinimidyl carbamate iodide (TAHS) and p-dimethylaminoanilyl-N-hydroxysuccinimidyl carbamate (DAHS). The larger the mass number difference, the better and, with regard to a stable isotope for those labeling reagent and constituting atom, the relation of $^{13}C$ to $^{12}C$ is preferred.

Prior Art Concerning the Simultaneous Measurement of Plural Samples

In the analysis of compounds with amino group in plural samples, it is necessary to conduct the analysis corresponding to the numbers of the samples. In that case, error among the measurements or, in other words, precision is a problem. It has been widely known that, especially when a mass spectrometer is used as a detector, ionization efficiency is different for each sample and, when amounts of the compounds among the samples are compared, correction by means of an internal standard substance is essential.

In order to carry out the analysis more quickly, it is possible according to the present invention to provide an excellent method where plural samples are measured at the same time. It is also possible that the resulting analytical result is semi-quantitatively and visually expressed. For example, it is now possible to handle the data in large quantities by, for example, expressing as a DNA microarray in a visual manner.

To be more specific, one or more stable isotope atom(s) is/are introduced into O=C—NH—Ar which is a reagent part of the carbamate compound whereupon it is now possible to subject plural samples to an analysis at the same time using a reagent where physical and chemical properties are nearly the same being different only in terms of mass and further using a tandem mass spectrometer.

INDUSTRIAL APPLICABILITY

In accordance with the present invention, it is now possible that a compound with amino group such as amino acid and peptide is analyzed easily and conveniently in a highly sensitive manner with an enhancement of the selectivity by the use of a specific labeling reagent. Particularly by means of a mass spectrometry such as an MS/MS method, the aimed compound is able to be quantitatively analyzed. It is also possible that plural samples are measured simultaneously. There are also provided a labeling reagent for mass spectroscopy used therefor and a novel compound which is able to be used for the labeling reagent.

Consequently, the present invention is able to be widely used in industry, particularly in the fields of foods, pharmaceuticals, medical services and analytical instruments and, therefore, it is quite useful.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Example 1

Synthesis of p-dimethylaminoanilyl-N-hydroyxysuccinimidyl carbamate p-Dimethylaminoanilyl-N-hydroyxysuccinimidyl carbamate was synthesized according to the following procedures. N,N-Dimethylamino-p-phenylenediamine (Wako Pure Chemicals) (535 mg) (5 mmol) was dissolved in 25 mL of acetonitrile (Junsei Kagaku) and placed in a dropping funnel. N,N'-Disuccinimidyl (DSC) (Wako Pure Chemicals) (1.28 g) (5 mmol) was dissolved in 50 mL of acetonitrile and stirred. Into this solution a solution of N,N-dimethylamino-p-phenylenediamine was added dropwise over a period of 22 hours. After completion of the dropwise addition, the mixture was stirred for 2 hours and acetonitrile was evaporated from the reaction mixture. After dissolving in 5 mL of acetonitrile, the separated substance therefrom was filtered. The resulting amount was 597 mg (yield: 48%).

$^1$H-NMR spectrum (CD$_3$CN, ppm): δ 7.22 (d, 9.0 Hz, 2H), 6.72 (d, 9.0 Hz, 2H), 2.88 (s, 6H), 2.76 (s, 4H).

QTOFMS: m/z 278 [M+H]$^+$, Molecular formula: C$_{13}$H$_{16}$N$_3$O$_4$ (high resolution QTOFMS: m/z 278.1141, [M+H]$^+$, Δ−4.4 ppm).

Example 2

Synthesis of p-trimethylammonium anilyl-N-hydroxysuccinimidyl carbamate iodide p-Trimethylammonium anilyl-N-hydroxysuccinimidyl carbamate iodide was synthesized according to the following procedures. p-dimethylaminoanilyl-N-hydroxysuccinimidyl carbamate (264 mg) (1.1 mmol) was dissolved in a mixed solvent of 8 mL of acetonitrile and 2 mL of dichloromethane (Junsei Kagaku) and stirred. To this solution 0.4 mL (8 equivalents) of methyl iodide (Nakarai Tesk) was added, followed by stirring for 23 hours and the separated substance was filtered. The resulting amount was 354 mg (yield: 76%).

$^1$H-NMR spectrum (DMSO-d6, ppm): δ 7.97 (d, 8.4 Hz, 2H), 7.62 (d, 8.4 Hz, 2H), 3.58 (s, 9H), 2.83 (s, 4H).

QTOFMS: m/z 292 [M]$^+$, Molecular formula; C$_{14}$H$_{18}$N$_3$O$_4$ (high resolution QTOFMS: m/z 292.1297 [M]$^+$, Δ−2.9 ppm).

Example 3

Synthesis of 3-aminopyridyl carbamate

2-Aminopyridyl carbamate was synthesized according to the following procedures. 470 mg (5 mmol) of 3-aminopyridine (Wako Pure Chemicals) were dissolved in 25 mL of acetonitrile and placed in a dropping funnel. N,N'-Disuccinimidyl carbonate (DSC) (1.28 g) (5 mmol) was dissolved in 50 ml of acetonitrile followed by stirring. Into this solution a 3-aminopyridine solution was added dropwise over a period of 2 hours. After completion of the dropwise addition, the mixture was stirred for 21 hours and acetonitrile was evaporated from the reaction mixture. The resulting non-crystalline solid (112 mg) was dissolved in 2 mL of diethyl ether (Junsei Kagaku) and allowed to stand in a dark and cool place for 12 hours and the separated substance was filtered. The resulting amount was 32 mg (yield: 29%).

$^1$H-NMR spectrum (CDCl$_3$, ppm): δ 8.52 (d, 2.4 Hz, 1H), 8.33 (dd, 1.2 and 4.8 Hz, 1H), 8.03 (ddd, 1.2, 2.4 and 8.8 Hz, 1H), 7.32 (dd, 4.8 and 8.8 Hz, 1H), 2.9 (s, 4H).

QTOFMS: m/z 236 [M+H]$^+$, Molecular formula: C$_{10}$H$_9$N$_3$O$_4$ (high resolution QTOFMS: m/z 236.0671, [M+H]+, Δ−1.5 ppm).

Example 4

Synthesis of 1-naphthylamino-N-hydroxysuccinimidyl carbamate

1-Naphthylamino-N-hydroxysuccinimidyl carbamate [refer to N. Nimura, K. Iwaki, T. Kinoshita, K. Takeda and H. Ogura, *Anal. Chem.*, 58 (1986) 2372] was synthesized according to the following procedures. 1-Naphthylamine (ICN) (715 mg) (5 mmol) was dissolved in 25 mL of acetonitrile and placed in a dropping funnel. N,N×-Disuccinimidyl carbonate (DSC) (1.28 g) (5 mmol) was dissolved in 50 mL of acetonitrile followed by stirring. Into this solution a 1-naphthylamine solution was added dropwise over a period of 2 hours. After completion of the dropwise addition, the mixture was stirred for 18 hours and acetonitrile was evaporated from the reaction mixture to give 558 mg (yield: 28%) of the desired compound.

Example 5

Synthesis of Succinimidophenyl Carbamate (PAHS)

PAHS [refer to N. Nimura, K. Iwaki, T. Kinoshita, K. Takeda and H. Ogura, *Anal. Chem.*, 58 (1986) 2372] was synthesized according to the following procedures. Aniline (Wako Pure Chemicals) (467 mg) (5 mmol) was dissolved in 25 mL of acetonitrile and placed in a dropping funnel. N,N'-Disuccinimidyl carbonate (DSC) (1.28 g) (5 mmol) was dissolved in 50 mL of acetonitrile followed by stirring. Into this solution an aniline solution was added dropwise over a period of 2 hours. After completion of the dropwise addition, the mixture was stirred for 23 hours and acetonitrile was evaporated from the reaction mixture to give a desired compound as a mixture.

Example 6

Specific Procedures for Labeling of Amine Using an Aromatic Carbamate Compound

Due to the difference in polarity of the aromatic carbamate, the following two methods (reaction conditions) were used for the labeling of the compound with amino group.

(1) A borate buffer (0.2 M of borate and 5 mM of EDTA) (60 μL) was added to 20 μL of a standard amine solution as a sample containing a compound with amino group. A standard reagent solution (3 mg of a carbamate compound in 1 mL of acetonitrile of an HPLC grade) (20 μL) was added to the mixture. The resulting mixture was heated at 55° C. for 10 minutes.

(2) To 20 μL of a standard amine solution (20 μL) as a sample containing a compound with amino group were added 80 μL of a borate buffer (0.2 M of borate and 5 mM of EDTA) and 80 μL of acetonitrile. To this mixture were added 20 μL of a reagent solution (3 mg of a carbamate compound in 1 ml of acetonitrile of an HPLC grade). The resulting mixture was heated at 55° C. for 10 minutes.

A standard amino acid mixture, which was prepared in the same manner using an amino acid mixture solution as the above standard amine solution, was separated by means of a reversed column and introduced into a mass spectrometer. General conditions were as follows.
 a) HPLC: Ajilent HP 1100;
 b) Column: Develosil C30 UG 5 μm 4.6 mm I.D.×250 mm;
 c) Detector: Mass spectrometer Sciex API 365;
 d) Mobile phase:
 Mobile phase A: 0.2% AcOH
 Mobile phase B: 0.2% AcOH in CH$_3$CN; and
 e) Temperature: 40° C.

Example 7

Analytical Example 1

Using p-trimethylammoniumanilyl-N-hydroxysuccinimidyl carbamate iodide (TAHS), a labeled amino acid prepared according to the reaction condition of (1) mentioned in Example 6 above was separated by HPLC using a reversed phase column and detected by a selected reaction monitoring. A mobile phase B 0 min 0%→20 min 30% gradient was used or HPLC separation.

In a measurement by an SRM mode, mass (amino acid+ labeling reagent-HOSu) which is a labeled product of the designated amino acid by the first mass analyzer (Q1) and, in the second mass analyzer (Q3), fragment ion m/z=177 derived from the reagent was selected and detected. (HOSu means N-hydroxysuccinimide.)

In the case of Glu, for example, the following was used: Q1: m/z=324/Q3: m/z=177.

In the case of Arg, His, Lys and Cys however, divalent ion of the labeled amino acid was selected in Q1.

For example, in the case of Arg (bonded product with the reagent 1) the following settings were used: Q1: m/z=176/Q3: m/z=177 while, in the case of Lys (bonded product with the reagent 2), as Q1: m/z=250/Q3: m/z=177. Result of the analysis is given in FIG. 1.

Figure 1:
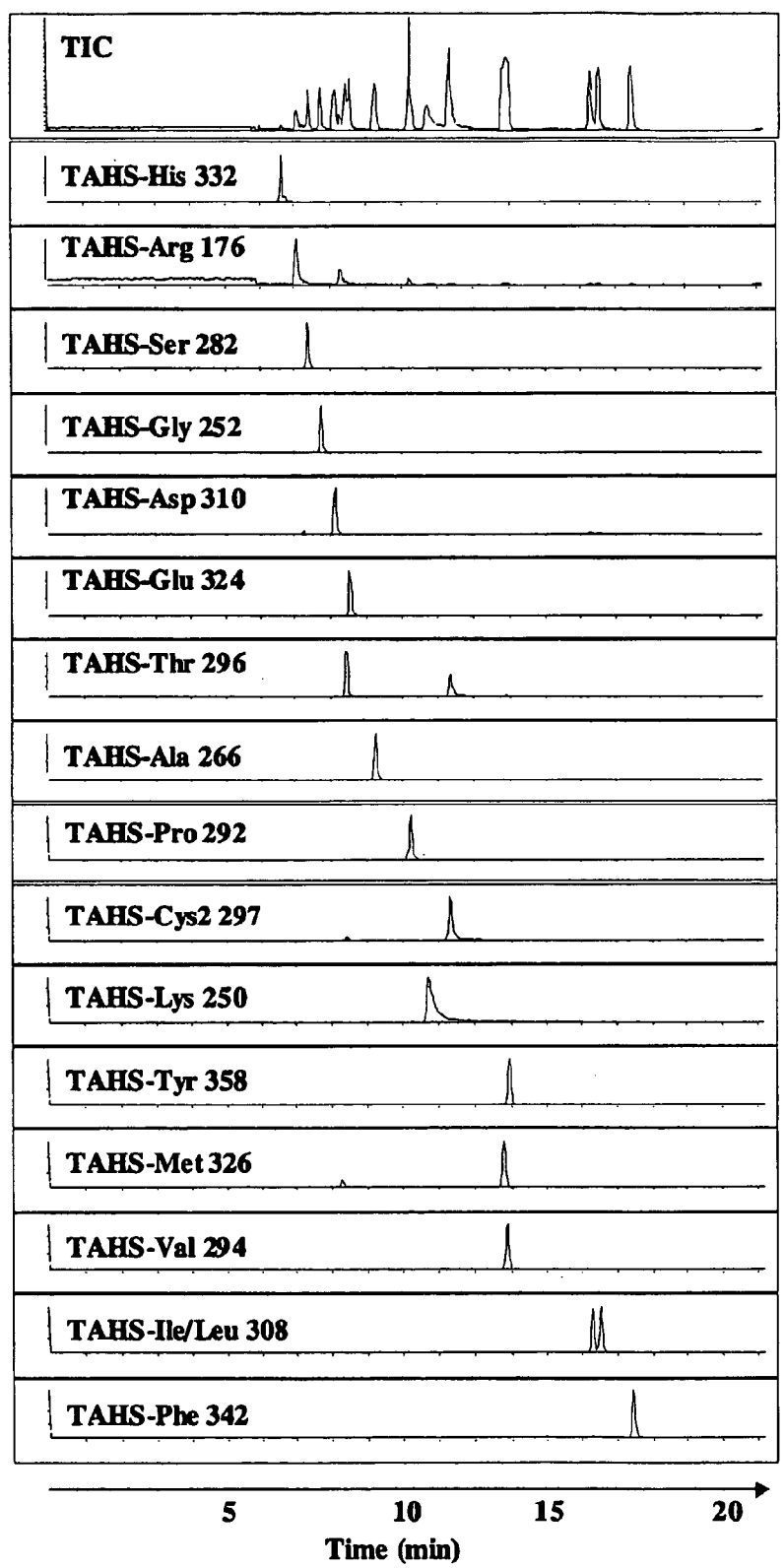
FIG. 1 shows the result of an SRM analysis of 17 TAHS-labeled amino acids.

As is apparent from the result of FIG. 1, it is possible to quantify the amino acid contained in the sample.

Example 8

Analytical Example 2

A labeled amino acid prepared by the reaction condition of (1) mentioned in Example 6 above using p-trimethylammoniumanilyl-N-hydroxysuccinimidyl carbamate iodide (TAHS) was separated by HPLC using a reversed column and detected by a precursor ion scan. A mobile phase B 0 min 0%→20 min 30% gradient was used for HPLC separation.

In regard to a measurement by a precursor ion scan mode, a mass range of m/z=100 to 600 was set in the first mass analyzer (Q1). In the second mass analyzer (Q3), there was set that fragment ion derived from the reagent as m/z=177. Result of the analysis is given in FIG. 2.

As is apparent from the result of FIG. 2, it is possible to know the mass of the amino acid contained in the sample.

Example 9

Analytical Example 3

A labeled amino acid prepared by the reaction condition of (2) mentioned in Example 6 above using p-dimethylaminoanilyl-N-hydroxysuccinimidyl carbamate (DAHS) was separated by HPLC using a reversed column and detected by a selected reaction monitoring. A mobile phase B 0 min 0%→20 min 30% gradient was used for HPLC separation.

The method for setting the mass spectrometer was the same as that in the above-mentioned Example 7 but, in Q3 where fragment ion derived from the reagent is to be detected, m/z was set as 163.

In the case of Glu, for example, the following settings were used for Q1: m/z=310/Q3: m/z=163.

In the case of Arg, His, Lys and Cys however, a divalent ion of the labeled amino acid was selected in Q1.

For example, in the case of Arg (bonded product with the reagent 1), the following settings were used: Q1: m/z=169/Q3: m/z=163 while, in the case of Lys (bonded product with the reagent 2), Q1: m/z=236I Q3: m/z=163. Result of the analysis is given in FIG. 3.

As is apparent from the result of FIG. 3, it is possible to quantify the amino acid contained in the sample.

Example 10

Analytical Example 4

A labeled amino acid prepared by the reaction condition of (1) mentioned in Example 6 above using 3-aminopyridyl carbamate (APDS) was separated by HPLC using a reversed column and detected by a selected reaction monitoring. A mobile phase B 0 min 0%→20 min 30% gradient was used for HPLC separation.

The method for setting the mass spectrometer was the same as that in the above-mentioned Example 7 but, in Q3 where fragment ion derived from the reagent is to be detected, m/z was set as 121.

In the case of Glu for example, the following settings were used: Q1: m/z=148/Q3: m/z=121.

In the case of Lys and Cys however, a divalent ion of the labeled amino acid is selected in Q1.

For example, in the case of Lys (bonded product with the reagent 2), the following settings were used: Q1: m/z=194/Q3: m/z=121. Result of the analysis is given in FIG. 4.

As is apparent from the result of FIG. 4, it is possible to quantify the amino acid contained in the sample.

Example 11

Analytical Example 5

A labeled amino acid prepared by the reaction condition of (1) mentioned in Example 6 above using p-aminoquinolyl-N-hydroxysuccinimidyl carbamate (AQC) separated by HPLC using a reversed column and detected by a selected reaction monitoring. A mobile phase B 0 min 0%→20 min 30% gradient was used for HPLC separation.

The method for setting the mass spectrometer was the same as that in Example 7 above but, in Q3 where fragment ion derived from the reagent is to be detected, m/z was set as 171.

In the case of Glu for example, the following settings were used for Q 1: m/z=318/Q3: m/z=171.

In the case of Arg, His, Lys and Cys however, a divalent ion of the labeled amino acid is selected in Q1.

For example, in the case of Arg (bonded product with the reagent 1) the following settings were used: Q1: m/z=178/Q3: m/z=171; while, in the case of Lys (bonded product with the reagent 2), the following settings were used: Q1: m/z=244/Q3: m/z=171. Result of the analysis is given in FIG. 5.

As is apparent from the result of FIG. 5, it is possible to quantify the amino acid contained in the sample.

Example 12

Analytical Example 6

A labeled amino acid prepared by the reaction condition of (2) mentioned in Example 6 above using 1-naphtylamino-N-hydroxysuccinimidyl carbamate (NAHS) separated by HPLC using a reversed column and detected by a constant neutral loss scan. A mobile phase B 0 min 10%→25 min 60%→25.1 min 80%→37 min 80% gradient was used for HPLC separation.

In regard to a constant neutral loss scan mode, a mass range of m/z=200 to 600 was set in the first mass analyzer (Q1). In the second mass analyzer (Q3), mass 170 corresponding to the reagent was set as a neutral loss and the mass range of m/z=200 to 600 was scanned. Result of the analysis is given in FIG. 6.

As is apparent from the result of FIG. 6, it is possible to know the mass of the amino acid contained in the sample.

Example 13

Analytical Example 7

A labeled amino acid prepared by the reaction condition of (2) mentioned in Example 6 above using PAHS was separated by HPLC using a reversed column and detected by a constant neutral loss scan. A mobile phase B 0 min 10%→25 min 60%→25.1 min 80%→37 min 80% gradient was used for HPLC separation.

In regard to a constant neutral loss scan mode, a mass range of m/z=150 to 400 was set in the first mass analyzer (Q1). In the second mass analyzer (Q3), mass 119 corresponding to the reagent was set as a neutral loss and the mass range of m/z=150 to 400 was scanned. Result of the analysis is given in FIG. 7.

Example 14

Analytical Example 8

A labeled amino acid prepared by the reaction condition of (1) mentioned in Example 6 above using p-trimethylammoniumanilyl-N-hydroxysuccinimidyl carbamate iodide (TAHS) separated by HPLC separation using a reversed column and detected by a selected reaction monitoring.

Develosil C30-UG (particle size: 3 μm; 4.6 I. D.×30 mm) was used as a separation column and mobile phase B 0 min→3 min=0%→56% gradient was used.

In regard to the measurement in an SRM mode, mass (amino acid+labeling reagent−HOSu) of the labeled product of the designated amino acid was selected in the first mass analyzer (Q1) while, in the second mass analyzer (Q3), the following setting was used: m/z=171 for fragment ion derived from the reagent.

In the case of Glu for example, the following settings were used: Q1: m/z=324/Q3: m/z=177.

In the case of Arg, Lys and Cys however, a divalent ion of the labeled amino acid is selected in Q1.

For example, in the case of Arg (bonded product with the reagent 1) the followings settings were used: Q1: m/z=176/Q3: m/z=177 while, in the case of Lys (bonded product with the reagent 2), as Q1: m/z=250/Q3: m/z=177. Result of the analysis is given in FIG. 8.

Depending upon the experimental conditions, a solution concentration for each amino acid was made 0.5 nmol/mL and the chromatogram when 10 μL were infused as shown in FIG. 8. The detection limit was 2 to 40 fmol.

Analysis of twenty kinds of amino acids could be finished within 3 minutes (8 minutes/cycle including the time for washing and equilibration).

Incidentally, it was not possible to discriminate Ile/Leu.

From the above, it is noted that, in the present invention, time for analysis is able to be greatly shortened using a TAHS reagent (cases for a short-time analysis).

Example 15

Measurement of Detection Limit

Detection limits of amino acids by a selected reaction monitoring method were determined as follows.

Detection limits of 17 kinds of amino acids (histidine, arginine, serine, glycine, aspartic acid, glutamic acid, threonine, alanine, proline, cystine, lysine, tyrosine, methionine, valine, leucine, isoleucine and phenylalanine) were determined by a selected reaction monitoring method.

The detection limit varies depending upon the type of the amino acid. The detection limit also varies with the mass spectrometer employed.

When an API 365 (Applied Biosystems) mass spectrometer was used as a detector, the detection limit was 2 to 40 fmol for p-trimethylammoniumanilyl-N-hydroxysuccinimidyl carbamate iodide (TAHS), 3 to 2000 fmol for p-dimethylaminoanilyl-N-hydroxysuccinimidyl carbamate (DAHS), 3 to 180 fmol for 3-aminopyridyl-N-hydroxysuccinimidyl carbamate (APDS) and 2 to 200 fmol for 6-aminoquinolyl-N-hydroxysuccinimide carbamate (AQC).

When an API 4000 (Applied Biosystems) mass spectrometer was used as a detector, the detection limit of the amino acid after being labeled with 6-aminoquinolyl-N-hydroxysuccinimide carbamate was 0.03 to 3 fmol. (fmol=10-15 mol) The result is given in the following Table 1.

TABLE 1

Detection Limit of Amino Acid by Each Labeling Reagent

| Amino Acid | TAHS[*1] | DAHS[*1] | APDS[*1] | AQC[*1] | AQC[*2] |
|---|---|---|---|---|---|
| His | 31 | 2353 | 138 | 222 | 1.2 |
| Arg | 39 | 148 | 143 | 15 | 2.7 |
| Ser | 8 | 6 | 12 | 23 | 0.15 |
| Gly | 6 | 13 | 15 | 7 | 0.10 |
| Asp | 4 | 17 | 10 | 9 | 0.14 |
| Glu | 4 | 17 | 10 | 7 | 0.091 |
| Thr | 9 | 11 | 67 | 8 | 0.063 |
| Ala | 4 | 7 | 7 | 3 | 0.066 |
| Pro | 2 | 26 | 14 | 6 | 0.052 |
| (Cys)$_2$ | 4 | 21 | 162 | 17 | 0.12 |
| Lys | 27 | 23 | 49 | 35 | 0.26 |
| Tyr | 3 | 4 | 3 | 2 | 0.031 |
| Met | 4 | 6 | 8 | 3 | 0.060 |
| Val | 4 | 7 | 5 | 3 | 0.055 |
| Ile | 2 | 3 | 6 | 2 | 0.24 |
| Leu | 2 | 3 | 6 | 2 | 0.23 |
| Phe | 3 | 3 | 3 | 3 | 0.039 |

Unit: fmol
[*1] A API 365 (Applied Biosystems) mass spectrometer was used
[*2] A API 4000 (Applied Biosystems) mass spectrometer of a type of was used From the results above, it is noted that a compound with amino group, such as an amino acid, is able to be analyzed (quantified) simply and conveniently with a high sensitivity.

Example 16

Isotope Ratio Analysis of a Standard Amino Acid Using an AQC Reagent

A labeled amino acid prepared by the reaction condition of (1) mentioned in Example 6 above was separated by HPLC using a reversed column using 6-aminoquinolyl-N-hydroxysuccinimidyl carbamate (AQC) (Waters) and detected by a selected reaction monitoring. A mobile phase B 0 min 0%→20 min 30% gradient was used for HPLC separation.

In regard to a measurement by an SRM mode, mass (amino acid+labeling reagent−HOSu) which is a labeled product of the designated amino acid was selected by the first mass analyzer (Q1) while, in the second mass analyzer (Q3), fragment ion m/z=171.1 derived from the reagent was selected and detected. (HOSu: N-hydroxysuccinimide)

Isotope ratio analysis was conducted where the resolving powers of the first mass analyzer (Q1) and the second mass analyzer (Q3) were under such a high resolving condition (Q1/Q3=unit/unit) that one mass unit was able to be discriminated.

For example, in the case of Leu, when the number of $^{13}$C in a molecule was taken into consideration, the following were used.

Q1: m/z=302.2(m,no$^{13}$C)/Q3: m/z=171.1
Q1: m/z=303.2(m+1, one$^{13}$C)/Q3: m/z=171.1
Q1: m/z=304.2(m+2, two$^{13}$C)/Q3: m/z=171.1
Q1: m/z=305.2(m+3, three$^{13}$C)/Q3: m/z=171.1
Q1: m/z=306.2(m+4, four$^{13}$C)/Q3: m/z=171.1
Q1: m/z=307.2(m+5, five$^{13}$C)/Q3: m/z=171.1
Q1: m/z=308.2(m+6, six$^{13}$C)/Q3: m/z=171.1

The result is given in Table 2.

TABLE 2

Isotope ratio of standard amino acid by an SRM method by means of LC/MS/MS (high resolving power) of a labeled amino acid using 6-aminoquinolyl-N-hydroxysuccinimidyl carbamate (AQC) (Waters) as a labeling agent

| Gly | C.V. | M.V. | S.D. | Ala | C.V. | M.V. | S.D. | Thr | C.V. | M.V. | S.D. |
|---|---|---|---|---|---|---|---|---|---|---|---|
| m | 96.9 | 97.2 | 0.5 | m | 95.8 | 95.8 | 0.1 | m | 94.5 | 93.5 | 2.0 |
| m+1 | 2.7 | 2.5 | 0.3 | m+1 | 3.7 | 3.8 | 0.3 | m+1 | 4.8 | 5.8 | 1.5 |
| m+2 | 0.4 | 0.3 | 0.2 | m+2 | 0.4 | 0.4 | 0.1 | m+2 | 0.7 | 0.6 | 0.6 |
| m+3 | 0.0 | 0.0 | 0.0 | m+3 | 0.0 | 0.0 | 0.0 | m+3 | 0.0 | 0.0 | 0.0 |
|   |   |   |   |   |   |   |   | m+4 | 0.0 | 0.0 | 0.0 |

| Phe | C.V. | M.V. | S.D. | Leu | C.V. | M.V. | S.D. | Met | C.V. | M.V. | S.D. |
|---|---|---|---|---|---|---|---|---|---|---|---|
| m | 89.6 | 90.1 | 1.2 | m | 92.6 | 92.7 | 0.6 | m | 89.0 | 90.4 | 1.5 |
| m+1 | 9.6 | 9.1 | 0.9 | m+1 | 6.8 | 6.7 | 0.4 | m+1 | 6.2 | 5.2 | 0.8 |
| m+2 | 0.8 | 0.7 | 0.3 | m+2 | 0.6 | 0.6 | 0.3 | m+2 | 4.5 | 4.3 | 0.8 |
| m+3 | 0.1 | 0.0 | 0.0 | m+3 | 0.0 | 0.0 | 0.0 | m+3 | 0.3 | 0.1 | 0.1 |
| m+4 | 0.0 | 0.0 | 0.0 | m+4 | 0.0 | 0.0 | 0.0 | m+4 | 0.0 | 0.0 | 0.0 |
| m+5 | 0.0 | 0.0 | 0.0 | m+5 | 0.0 | 0.0 | 0.0 | m+5 | 0.0 | 0.0 | 0.0 |
| m+6 | 0.0 | 0.0 | 0.0 | m+6 | 0.0 | 0.0 | 0.0 |   |   |   |   |
| m+7 | 0.0 | 0.0 | 0.0 |   |   |   |   |   |   |   |   |
| m+8 | 0.0 | 0.0 | 0.0 |   |   |   |   |   |   |   |   |
| m+9 | 0.0 | 0.0 | 0.0 |   |   |   |   |   |   |   |   |

C.V.: Calculated Value
M.V.: Measured Value
S.D.: Standard Deviation

Based on the foregoing, it is understood that in accordance with the present invention an isotope of a compound with amino group is able to be measured easily and conveniently with a high sensitivity. It is also noted that the isotope ratio was able to be determined with a high sensitivity without a calculation for correction.

Example 17

Identification of Phenylalanine

The following experimental operation was performed with a supposition that mass, fragment ion and composition formula of phenylalanine were unknown. Hereinafter, phenylalanine used as a specimen was expressed as an unknown compound and the steps until it was identified as phenylalanine will be mentioned.

The m/z of the unknown compound was determined as 336 and, in the apparatus where a precise mass was able to be measured (quadrupole mass spectrometer of a time of flight type); the precise mass of the aimed labeled unknown compound was determined to be 336.1373. From the resulting precise mass, a candidate for the composition formula of the unknown compound was $C_9H_{11}NO_2$ (a composition formula nearest the theoretical value=error was minimum). On the basis of such information, a search was conducted for a candidate compound using a database of the KEGG (http://www.genome.adjp/kegg/) and phenylalanine and benzocaine were identified as candidate substances for the unknown compound.

Example 18

Synthesis of p-trimethylammonium anilyl-N-hydroxysuccinimidyl carbamate iodide-d3 p-Trimethylammonium anilyl-N-hydroxysuccinimidyl carbamate iodide-d3 was synthesized according to the following procedures. p-Dimethylaminoanilyl-N-hydroxysuccinimidyl carbamate (264 mg) (1.1 mmol) was dissolved in a mixed solvent of 8 mL of acetonitrile and 2 mL of dichloromethane (Junsei Kagaku) followed by stirring. To this solution 0.4 mL (8 equivalents) of methyl iodide-d3 (Nippon Sanso) was added and subsequently stirred for 50 hours and the separated substance was filtered.

Example 19

Analytical Example 9

A reaction solution containing a labeled amino acid (amino acid concentration: 5 nmol/mL) was prepared by the reaction condition of (1) mentioned in Example 6 above using p-trimethylammoniumanilyl-N-hydroxysuccinimidyl carbamate iodide-d3 (TAHS-d3). Further, a labeled amino acid (amino acid concentration: 10 nmol/mL) was prepared by the reaction condition of (1) mentioned in Example 6 above using p-trimethylammoniumanilyl-N-hydroxysuccinimidyl carbamate iodide (TAHS). These labeled amino acids were mixed, separated by HPLC using a reverse phase column and detected by a selected reaction monitoring. A mobile phase B 0 min 0%→20 min 30% gradient was used for HPLC separation.

In regard to a measurement by an SRM mode, mass (amino acid+labeled reagent−HOSu) of a labeled product of the designated amino acid was selected by the first mass analyzer (Q1) while, in the second mass analyzer (Q3), fragment ion derived from the reagent was selected and detected.

For example, in the case of Phe, the followings were used.

Q1: m/z=345/Q3: m/z=180 for Phe which was labeled with TAHS-d3 and

Q1: m/z=342/Q3: m/z=177 for Phe which was labeled with TAHS.

The result is given in FIG. 9.

Example 20

Analytical Example 10

An analytical result of a reaction mixture comprising a sample A which was prepared by the reaction condition of (1) mentioned in Example 6 above using p-trimethylammoniumanilyl-N-hydroxysuccinimidyl carbamate iodide-d3 (TAHS-d3) and a sample B, which was prepared by the reaction condition of (1) mentioned in Example 6 above using p-trimethylammonium anilyl-N-hydroxysuccinimidyl carbamate iodide (TAHS), is expressed, for example, on a metabolism map in a visual manner and is given in FIG. 10.

As a result thereof, it is now possible for the relative and semi-quantitative result of the difference among the states of plural samples to be visually expressed by a simple and convenient operation without carrying out the sensitivity correction, etc. among the analyses.

Numerous modifications and variations on the present invention are possible in light of the above teachings. It is, therefore, to be understood that within the scope of the accompanying claims, the invention may be practiced otherwise than as specifically described herein.

The invention claimed is:

1. A carbamate compound represented by the formula (1) comprising a stable isotope element on at least one atom contained in the structure O=C—NH—Ar

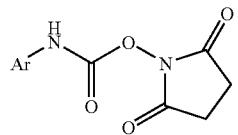

(1)

wherein Ar is a carbocyclic compound or a heterocyclic compound having an aromaticity where the aromatic ring may have one or more substituent(s), and wherein in the bond between Ar group and nitrogen atom of a carbamate group, a carbon atom within the ring in the Ar group is bound to a nitrogen atom of the carbamate group, whereby the carbamate compound may be in a form of a salt with the proviso that the stable isotope element is not the hydrogen atom bound to a nitrogen atom of the carbamate group.

2. The carbamate compound according to claim 1, wherein Ar is selected from the group consisting of phenyl group, naphthyl group, anthryl group, pyridyl group, pyrazyl group, quinolyl group, acridyl group, and coumaryl group.

3. The carbamate compound according to claim 1, wherein Ar is selected from the group consisting of a substituted phenyl group, a substituted naphthyl group, a substituted anthryl group, a substituted pyridyl group, a substituted pyrazyl group, a substituted quinolyl group, a substituted acridyl group, and a substituted coumaryl group;

wherein when Ar is substituted, the substituent is selected from the group consisting of alkyl group, aromatic group, halogen atom, carboxyl group, hydroxyl group, nitro group, diazo group, cyano group, alkoxy group, acyl group, sulfonic acid group, phosphoric acid group, guanidyl group, dialkylamino group and trialkylammonium group.

4. The carbamate compound according to claim 1, wherein the stable isotope is selected from $^{13}$C, $^{2}$H (D), $^{15}$N and $^{18}$O.

5. A method for analyzing an amino acid or derivative thereof in a sample containing at least one amino acid or derivative thereof by means of mass spectrometry, comprising labeling said amino acid or derivative thereof in said sample by reacting said amino acid or derivative thereof with the carbamate compound according to claim 1 for a time and under conditions suitable to facilitate said labeling providing a sample containing an amino acid or derivative thereof labeled with a carbamate compound having one or more of stable isotope, and subjecting the labeled compound to mass spectrometry.

6. The method according to claim 5, wherein said mass spectrometry is tandem mass spectrometry.

7. The method according to claim 6, wherein said tandem mass spectrometry is selected from the group consisting of a selected reaction monitoring method, a precursor ion scan method and a constant neutral loss scan method.

8. The method according to claim 7, wherein said tandem mass spectrometry is a selected reaction monitoring method.

9. The method according to claim 8, further comprising determining an isotope ratio of the amino acid or derivative thereof on the basis of the results obtained from said tandem mass spectrometry.

10. The method according to claim 5, wherein said sample containing an amino acid or derivative thereof labeled with a carbamate compound having one or more of stable isotope is mixed with another sample containing an amino acid or derivative thereof labeled with a carbamate compound having the same structure as the isotope-labeled carbamate compound which does not contain an isotopic label and analyzing the mixed sample by tandem mass spectrometry.

11. The method according to claim 10, wherein said carbamate compound containing no stable isotope is not synthetically introduced or follows a ratio existing in nature.

12. The method according to claim 10, wherein said isotope-labeled carbamate compound contains $^{12}$C and/or $^{13}$C.

13. The method according to claim 10, wherein the method comprises a method where the result from said tandem mass spectrometry is expressed in a relative, semi-quantitative and visual manner.

14. A carbamate compound represented by formula (1)

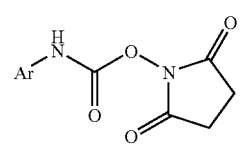

(1)

wherein Ar bound to a nitrogen atom of a carbamate group is
a carbocyclic compound or heterocyclic compound residue having an
aromaticity where a polar substituent is bound to the ring, or
a pyridyl group or a pyrazyl group where a polar substituent is not bound to the ring, and
wherein in the bond between the Ar group and a nitrogen atom in the carbamate group, a carbon atom within the ring in the Ar group is bound to a nitrogen atom of the carbamate group, whereby the carbamate compound may be in a form of a salt, and
wherein said polar substituent is selected from the group consisting of sulfonic acid group, guanidyl group, phosphoric acid group, dialkylamino group and trialkylammonium group.

15. The carbamate compound according to claim 14, wherein said carbocyclic compound or heterocyclic compound residue is selected from the group consisting of phenyl group, naphthyl group, anthryl group, pyridyl group, and pyrazyl group.

16. The carbamate compound according to claim 14, wherein the alkyl groups in the dialkylamino group and trialkylammonium group each independently is an alkyl group having 1 to 5 carbon(s).

17. A method for analyzing an amino acid or derivative thereof in a sample containing at least one amino acid or derivative thereof by means of mass spectrometry, comprising
labeling said amino acid or derivative thereof in said sample by reacting said amino acid or derivative thereof with a carbamate compound represented by formula (1) for a time and under conditions suitable to facilitate said labeling providing a sample containing an amino acid or derivative thereof labeled with a carbamate compound, and
subjecting the labeled compound to mass spectrometry,
wherein said carbamate compound represented by formula (1) is defined as follows:

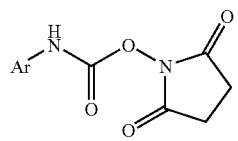

(1)

wherein Ar bound to a nitrogen atom of a carbamate group is
a carbocyclic compound or heterocyclic compound residue having an
aromaticity where a polar substituent is bound to the ring, or
a pyridyl group or a pyrazyl group where a polar substituent is not bound to the ring, and
wherein in the bond between the Ar group and a nitrogen atom in the carbamate group, a carbon atom within the ring in the Ar group is bound to a nitrogen atom of the carbamate group, whereby the carbamate compound may be in a form of a salt.

18. The method according to claim 17, wherein said mass spectrometry is tandem mass spectrometry.

19. The method according to claim 18, wherein said tandem mass spectrometry is selected from the group consisting of a selected reaction monitoring method, a precursor ion scan method and a constant neutral loss scan method.

20. The method according to claim 19, wherein said tandem mass spectrometry is a selected reaction monitoring method.

21. The method according to claim 20, wherein said carbamate compound represented by formula (1) contains a stable isotope element on at least one atom contained in the structure O=C—NH—Ar with the proviso that the stable isotope element is not the hydrogen atom bound to a nitrogen atom of the carbamate group and wherein said method further comprises determining an isotope ratio of the amino acid or derivative thereof on the basis of the results obtained from said tandem mass spectrometry.

22. The method according to claim 17, wherein said sample containing an amino acid or derivative thereof labeled with said carbamate compound of formula (1) is mixed with another sample containing an amino acid or derivative thereof labeled with a carbamate compound having one or more of stable isotope, wherein the carbamate compound is the same in both samples, and analyzing the mixed sample by tandem mass spectrometry.

23. The method according to claim 22, wherein said carbamate compound containing no stable isotope is not synthetically introduced or follows a ratio existing in nature.

24. The method according to claim 22, wherein said isotope-labeled carbamate compound contains $^{12}$C and/or $^{13}$C.

25. The method according to claim 22, wherein the method comprises a method where the result from said tandem mass spectrometry is expressed in a relative, semi-quantitative and visual manner.

26. A method for analyzing an amino acid or derivative thereof in a sample containing at least one amino acid or derivative thereof by means of mass spectrometry, comprising
labeling said amino acid or derivative thereof in said sample by reacting said amino acid or derivative thereof with a carbamate compound represented by formula (1)

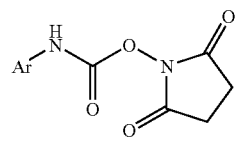

(1)

wherein Ar is a carbocyclic compound or a heterocyclic compound residue having an aromaticity where the aromatic ring may have one or more substituents, and
wherein in the bond between Ar group and a nitrogen atom in the carbamate group, a carbon atom within the ring in Ar group is bound to a nitrogen atom of the carbamate group, whereby the carbamate compound may be in a form of a salt, and
subjecting the labeled amino acid or derivative thereof to tandem mass spectrometry wherein said tandem mass spectrometry is a selected reaction monitoring method, and
wherein said carbamate compound represented by formula (1) contains a stable isotope element on at least one atom contained in the structure O=C—NH—Ar with the proviso that the stable isotope element is not the hydrogen atom bound to a nitrogen atom of the carbamate group and wherein said method further comprises a step of determining an isotope ratio of the amino acid or derivative thereof on the basis of the results obtained from said tandem mass spectrometry.

27. The method according to claim 26, wherein Ar is selected from the group consisting of phenyl group, naphthyl group, anthryl group, pyridyl group, pyrazyl group, quinolyl group, acridyl group and coumaryl group.

28. The method according to claim 27, wherein Ar is substituted and the substituent is selected from the group consisting of alkyl group, aromatic group, halogen atom, carboxyl group, hydroxyl group, nitro group, diazo group, cyano group, alkoxy group, acyl group, sulfonic acid group, phosphoric acid group, guanidyl group, dialkylamino group and trialkylammonium group.

29. A method for analyzing an amino acid or derivative thereof in a sample containing at least one amino acid or derivative thereof by means of mass spectrometry, comprising labeling said amino acid or derivative thereof in said sample by reacting said amino acid or derivative thereof with a carbamate compound represented by formula (1)

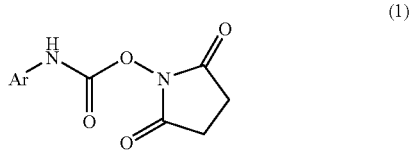
(1)

wherein Ar is a carbocyclic compound or a heterocyclic compound residue having an aromaticity where the aromatic ring may have one or more substituents, and wherein in the bond between Ar group and a nitrogen atom in the carbamate group, a carbon atom within the ring in Ar group is bound to a nitrogen atom of the carbamate group, whereby the carbamate compound may be in a form of a salt, and subjecting the labeled amino acid or derivative thereof to tandem mass spectrometry wherein said tandem mass spectrometry is a selected reaction monitoring method, and wherein said sample containing an amino acid or derivative thereof labeled with a carbamate compound is mixed with another sample containing an amino acid or derivative thereof labeled with said carbamate compound of formula (1) having one or more of stable isotope, wherein the carbamate compound is the same in both samples, and analyzing the mixed sample by tandem mass spectrometry.

30. The method according to claim 29, wherein said carbamate compound containing no stable isotope is not synthetically introduced or follows a ratio existing in nature.

31. The method according to claim 29, wherein said isotope-labeled carbamate compound contains $^{12}C$ and/or $^{13}C$.

32. The method according to claim 29, wherein the method comprises a method where the result from said tandem mass spectrometry is expressed in a relative, semi-quantitative and visual manner.

33. The method according to claim 29, wherein Ar is selected from the group consisting of phenyl group, naphthyl group, anthryl group, pyridyl group, pyrazyl group, quinolyl group, acridyl group and coumaryl group.

34. The method according to claim 33, wherein Ar is substituted and the substituent is selected from the group consisting of alkyl group, aromatic group, halogen atom, carboxyl group, hydroxyl group, nitro group, diazo group, cyano group, alkoxy group, acyl group, sulfonic acid group, phosphoric acid group, guanidyl group, dialkylamino group and trialkylammonium group.

35. A carbamate compound selected from the group consisting of p-Dimethylaminoanilyl-N-hydroxysuccinimidyl carbamate, 3-aminopyridyl-N-hydroxysuccinimidyl carbamate, p-trimethylammonium anilyl-N-hydroxysuccinimidyl carbamate iodide, and aminopyrazyl-N-hyroxysuccinimidyl carbamate.

* * * * *